United States Patent [19]

Skuballa et al.

[11] 4,191,694

[45] Mar. 4, 1980

[54] PROSTAGLANDIN-$I_2$ DERIVATIVES

[75] Inventors: Werner Skuballa; Bernd Radüchel; Norbert Schwarz; Helmut Vorbrüggen; Bernd Müller; Gerda Mannesmann; Olaf Loge; Ekkehardt Schillinger; Jorge Casals-Stenzel, all of Berlin, Fed. Rep. of Germany

[73] Assignee: Schering Aktiengesellschaft, Berlin and Bergkamen, Fed. Rep. of Germany

[21] Appl. No.: 928,126

[22] Filed: Jul. 26, 1978

[30] Foreign Application Priority Data

Jul. 29, 1977 [DE] Fed. Rep. of Germany ....... 2734791

[51] Int. Cl.² .................. C07D 307/93; A61K 31/34
[52] U.S. Cl. ............................. 260/346.22; 424/275;
424/283; 424/285; 260/326.36; 260/345.7 P;
260/346.73; 542/426; 546/242; 546/269;
424/263; 424/267; 549/28; 549/60
[58] Field of Search .............. 260/346.22, 346.73,
260/345.7 P, 326.36, 327 TH, 332.2 R;
542/426; 424/285; 546/242, 269

[56] References Cited

PUBLICATIONS

Corey et al., J. Am. Chem. Soc. 99: 2006 (1977).

*Primary Examiner*—Rotman Alan L.
*Assistant Examiner*—Bernard Dentz
*Attorney, Agent, or Firm*—Millen & White

[57] ABSTRACT

Prostane derivatives of the formula

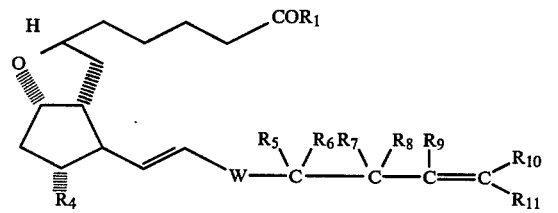

wherein
$R_1$ is $OR_2$ or $NHR_3$;
$R_2$ is hydrogen, $C_{1-10}$ alkyl, $C_{4-10}$ cycloalkyl, $C_{6-10}$ aryl, or a 5 or 6 membered heterocyclic ring having 1–3 hetero atoms selected from O, N and S;
$R_3$ is the residue of a hydrocarbon carboxylic or sulfonic acid of 1–15 carbon atoms;
W is (a) an OH-substituted methylene group, (b) a

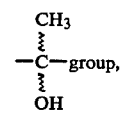

wherein the OH-groups in (a) or (b) can be in the α- or β-position, or (c) such a group wherein the H atom of the OH group is replaced by the residue of a hydrocarbon carboxylic or sulfonic acid of 1–15 carbon atoms or by a conventional etherifying OH-blocking group;
$R_4$ is OH or hydroxy whose H atom is replaced as defined for W; and
$R_5$, $R_6$, $R_7$, $R_8$, $R_9$, $R_{10}$ and $R_{11}$ each independently is hydrogen or alkyl of 1–5 carbon atoms; or $R_9$ and $R_{10}$ together represent a direct bond; and, when $R_{11}$ is alkyl, $R_{10}$ can also be chlorine;
and, for a derivative wherein $R_2$ is hydrogen, the salts thereof with physiologically compatible bases, have improved prostaglandin activity.

60 Claims, No Drawings

PROSTAGLANDIN-I₂ DERIVATIVES

BACKGROUND OF THE INVENTION

The present invention relates to novel prostaglandin I₂ derivatives, processes for the preparation thereof, as well as their use as medicinal agents.

A recently issued publication in "Nature" [London] 263: 663 (1976) discloses that prostaglandin-I₂ (PGI₂) compounds inhibit the ADP-induced blood platelet aggregation. Furthermore, PGI₂ has a blood-pressure-lowering effect due to its dilating action on the smooth musculature of arteries.

However, PGI₂ does not possess the stability required for a medicinal agent. Thus, its half-life at physiological pH values and at room temperature is only a few minutes.

Corey et al [JACS 99:2006 (1977)] did succed in producing more stable PGI₂ derivatives by saturating the 5,6-double bond in PGI₂; however, the biological spectrum of the effectiveness of these derivatives became weaker.

Thus, there is still a need for stable PGI₂ derivatives having a suitable effectiveness and selectivity.

SUMMARY OF THE INVENTION

Accordingly, it is an object of this invention to provide such PGI₂ derivatives which are stable, have a longer duration of activity, a greater selectivity and higher effectiveness.

Upon further study of the specification and appended claims, further objects and advantages of this invention will become apparent to those skilled in the art.

These objects have been attained by the present invention by providing prostane derivatives of Formula I

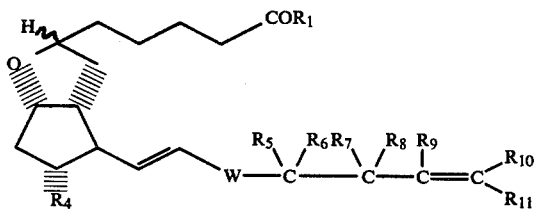

wherein
- $R_1$ is $OR_2$ or $NHR_3$;
- $R_2$ is hydrogen, alkyl, cycloalkyl, aryl or a heterocyclic residue;
- $R_3$ is an acid residue;
- $W$ is a free, or functionally modified, hydroxy-substituted, methylene group or a free or functionally modified

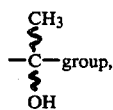

wherein the OH-group can be in the α or β-position;
- $R_4$ is a free or functionally modified hydroxy group; and
- $R_5, R_6, R_7, R_8, R_9, R_{10}$ and $R_{11}$ each independently is hydrogen or alkyl of 1-5 carbon atoms; or $R_9$ and $R_{10}$ together represent a direct bond; or when $R_{11}$ is alkyl, $R_{10}$ can also be chlorine;

and, for the compound wherein $R_2$ is hydrogen, the salts thereof with physiologically compatible bases.

The compounds of this invention exhibit a blood-pressure-lowering effect, a diuretic activity, and a regulatory activity towards disturbances of the heart rhythm. In addition, these compounds are suitable for inhibiting thrombocyte aggregation.

DETAILED DISCUSSION

It has now been found that it is possible to obtain a longer duration of activity, a greater selectivity, and a higher effectiveness in PGI₂ derivatives by the introduction of multiple [unsaturation] bonds and, optionally, alkyl groups in the lower chain of a 5,6-dihydro-PGI₂ as indicated by formula I above.

Suitable alkyl groups $R_2$ include straight-chain or branched alkyl groups of 1–10, preferably 1–4, carbon atoms, e.g., methyl, ethyl, propyl, butyl, isobutyl, tert-butyl, pentyl, neopentyl, heptyl, hexyl and decyl.

The alkyl groups $R_2$ can optionally be mono- to polysubstituted (e.g., 1–3 substituents, preferably 1 substitutent by halogen, $C_{1-4}$ alkoxy, optionally substituted $C_{6-10}$ aryl, $diC_{1-4}$ alkylamines and $triC_{1-4}$ alkylammonium. Suitably substituted aryl groups are those listed below. Examples of such substituents include fluorine, chlorine, bromine, phenyl, dimethylamine, diethylamine, methoxy and ethoxy.

Preferred alkyl groups $R_2$ are those of 1–4 carbon atoms, e.g., dimethylaminopropyl, isobutyl and butyl.

Suitable aryl groups $R_2$ having 6–10, preferably 6 carbon atoms, include substituted as well as unsubstituted aryl groups, e.g., phenyl, 1-naphthyl, and 2-naphthyl, each of which can be substituted by 1–3 halogen atoms, phenyl, 1–3 alkyl groups each of 1–4 carbon atoms, chloromethyl, fluoromethyl, trifluoromethyl, carboxyl, hydroxy, or alkoxy of 1–4 carbon atoms. Preferred substituents are those in the 3- and 4-positions of the phenyl ring, e.g., by fluorine, chlorine, alkoxy, or trifluoromethyl, or in the 4-position by hydroxy.

The cycloalkyl group $R_2$ can contain 4–10, preferably 5 or 6 carbon atoms in the ring. The rings can be substituted by alkyl groups of 1–4 carbon atoms. The total number of carbon atoms in each substituted cycloalkyl should be 4–10, preferably 4–8. Examples in this connection include cyclopentyl, cyclohexyl, methylcyclohexyl, and adamantyl.

Suitable heterocyclic groups $R_2$ include 5- and 6-membered heterocycles containing at least one hetero atom, i.e., 1–3, preferably 1 hetero atom, preferably nitrogen, oxygen or sulfur. Examples are 2-furyl, 2-thienyl, 2-pyridyl, 3-pyridyl, 4-pyridyl and others. The heterocyclic rings can be aromatic or aliphatic.

Suitable acid residues $R_3$ include physiologically compatible acid residues. Preferred acids are organic hydrocarbon carboxylic acids and sulfonic acids of 1–15 carbon atoms of the aliphatic, cycloaliphatic, aromatic, aromatic-aliphatic, and heterocyclic series. These acids can be saturated, unsaturated and/or monobasic or polybasic and/or unsubstituted or substituted in conventional fashion. Examples of substituents include $C_{1-4}$ alkyl, hydroxy, $C_{1-4}$ alkoxy, oxo, amino, or halogen.

Suitable carboxylic acids include, for example: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acid substituted by halogen, trifluoromethyl, hydroxy, alkoxy, or carboxy groups, nicotinic acid, isonicotinic acid, furan-2-carboxylic acid and cyclopentylpropionic acid. Especially preferred acyl residues are those of up to 10 carbon atoms.

Examples of suitable sulfonic acids include methanesulfonic acid, ethanesulfonic acid, isopropylsulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)aminosulfonic acid, N,N-diisobutylaminosulfonic acid, N,N-dibutylaminosulfonic acid and pyrrolidino-, piperidino-, piperazino-, N-methylpiperazino- and morpholinosulfonic acids.

As is evident from the diverse nature of the illustrative carboxylic and sulfonic acids named above, the exact structure of the acid residue is not critical. Therefore, contemplated equivalents of these preferred hydrocarbon carboxylic and sulfonic acids are those other types of acids named above, e.g., the heterocyclic acids.

Suitable alkyl groups $R_5$, $R_6$, $R_7$, $R_8$, $R_9$, $R_{10}$, $R_{11}$ include straight-chain and branched alkyl residues of 1-5 carbon atoms, e.g., methyl, ethyl, propyl, isopropyl, butyl, isobutyl, tert-butyl, pentyl, isopentyl, and neopentyl. The methyl and ethyl groups are preferred.

The hydroxy groups $R_4$ and W can be functionally modified, for example, by etherification or esterification, wherein the free or modified hydroxy groups in W can be in the α- or β-position. Free hydroxy groups are preferred.

The conventional residues known to those skilled in the art can be used as the ether and acyl residues, e.g., as disclosed in Mc. Omie Ed., Protective Groups in Organic Chemistry, Plenum Press, N.Y. 1973, which is incorporated by reference herein.

Ether residues which can be readily split off, i.e., conventional ether blocking groups, are preferred, e.g., the tetrahydropyranyl, tetrahydrofuranyl, α-ethoxyethyl, trimethylsilyl, dimethyl-tert-butylsilyl and tri-p-benzylsilyl residues. Suitable preferred acyl residues are the acid residues indicated for $R_3$; preferred examples include acetyl, propionyl, butyryl and benzoyl.

Suitable for the formation of physiologically compatible salts are the conventional inorganic and organic bases known to persons skilled in the art. Examples include alkali metal hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The invention furthermore relates to a process for the preparation of the novel prostane derivatives of general Formula I, characterized in that, in a manner known per se, a compound of general Formula II

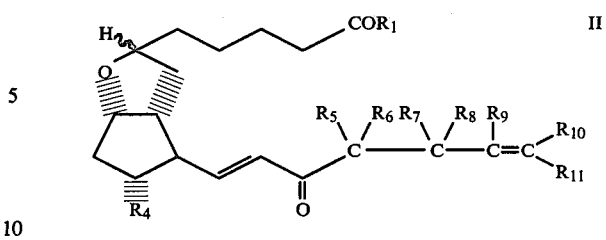

wherein $R_1$, $R_4$, $R_5$, $R_6$, $R_7$, $R_8$, $R_9$, $R_{10}$ and $R_{11}$ have the above-indicated meanings, is, optionally after blocking any free hydroxy groups present, (a) reduced, or
(b) reacted with $CH_3$-Mg-Br or with $CH_3$-Li; or
(c) a compound of general Formula IV

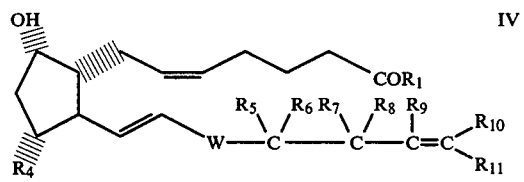

wherein $R_1$, $R_4$, $R_5$, $R_6$, $R_7$, $R_8$, $R_9$, $R_{10}$, $R_{11}$ and W have the above-indicated meanings, is reacted with a mercury(II) salt of an organic carboxylic acid and with a reducing agent; and the process products obtained according to (a), (b) or (c) are optionally thereafter, in any desired sequence, separated into the epimers; blocked hydroxy groups are liberated and/or free hydroxy groups are esterified or etherified; an esterified carboxy group is saponified; or a carboxy group is esterified; a carboxy group is reacted with compounds of general Formula III $$O=C=N-R_3 \qquad III$$

wherein $R_3$ has the above-indicated meanings; or a carboxy group is converted into a salt with a physiologically compatible base.

The reduction of the carbonyl group to obtain the compounds of general Formula I according to process (a) is conducted with customary reducing agents, e.g. sodium borohydride, lithium tri-tert.-butoxyaluminum hydride, zinc borohydride, aluminum isopropylate in the presence of an alcohol, or potassium tri-sec.-butyl-borohydride, preferably with sodium borohydride or zinc borohydride, at temperatures of between −70° and +50° C., preferably −40° to +20° C. Suitable solvents for this reaction are, depending on the reducing agent employed: methanol, ethanol, isopropanol, diethyl ether, dioxane, tetrahydrofuran, dimethoxyethane. During the reduction with sodium borohydride, methanol, ethanol or isopropanol is preferably utilized. The reduction with zinc borohydride is preferably conducted in dimethoxyethane and/or diethyl ether.

The reaction of the carbonyl group in compounds of general Formula II with methylmagnesium bromide or methyllithium takes place conventionally in an inert solvent or solvent mixture, e.g. diethyl ether, tetrahydrofuran, dioxane, dimethoxyethane, preferably diethyl ether. The reaction is accomplished at temperatures of between −100° and +60° C., preferably at −60° to +30° C.

The thus-produced mixture of epimers can be separated in the usual way by column or layer chromatography.

The reaction of the compound according to general Formula IV to obtain the compounds of general Formula I takes place by following conventional methods. One example is the reaction of IV with a mercury(II) salt and subsequent reduction of the intermediary mercury compound.

A preferred embodiment resides in reacting the compounds of general Formula IV with mercury salts of an organic carboxylic acid, e.g. mercury acetate, mercury trifluoroacetate, mercury propionate, etc. Alkali or alkaline earth carbonate is optionally added, for example calcium carbonate. The reaction takes place, for example, at temperatures of between +50° and −70° C., preferably between +30° and −20° C. in an inert solvent, such as, for example, tetrahydrofuran, glyme, diglyme, dioxane, etc., preferably in tetrahydrofuran. The customary reducing agents can be used for the reduction of the intermediary mercury compound, e.g. sodium borohydride, amalgam, etc.

The saponification of the prostaglandin esters is effected according to methods known to those skilled in the art, for example with basic catalysts or by reductive splitting reaction.

The introduction of the ester group —$OR_2$ for $R_1$, wherein $R_2$ represents an alkyl group of 1–10 carbon atoms, takes place by following methods known to persons skilled in the art. The carboxy compounds are reacted, for example, in a conventional manner with diazohydrocarbons. The esterification with diazohydrocarbons is conducted, for example, by combining a solution of the diazohydrocarbon in an inert solvent, preferably in diethyl ether, with the carboxyl compound in the same or another inert solvent, e.g. methylene chloride. After the reaction is terminated within 1–30 minutes, the solvent is removed, and the ester is purified in the usual way. Diazoalkanes are either known or can be produced according to conventional methods [Org. Reactions, 8:389–394 (1954)].

The introduction of the ester group —$OR_2$ for $R_1$, wherein $R_2$ represents a substituted or unsubstituted aryl group, takes place according to methods known to those skilled in the art. For example, the carboxy compounds are reacted with the corresponding arylhydroxy compounds with dicyclohexylcarbodiimide in the presence of a suitable base, e.g. pyridine or triethylamine, in an inert solvent. Suitable solvents are methylene chloride, ethylene chloride, chloroform, ethyl acetate, tetrahydrofuran, preferably chloroform. The reaction is conducted at temperatures of between −30° and +50° C., preferably at +10° C.

The prostaglandin derivatives of general Formula I with $R_1$ signifying a hydroxy group can be converted into salts with suitable quantities of the corresponding inorganic bases, under neutralization. For example, by dissolving the corresponding PG acids in water containing the stoichiometric amount of the base, the solid inorganic salt is obtained after the water has been removed by evaporation or after adding a water-miscible solvent, e.g. alcohol or acetone.

For the preparation of an amine salt, which takes place in the usual way, the PG acid is dissolved, for example, in a suitable solvent, e.g. ethanol, acetone, diethyl ether, or benzene, and at least the stoichiometric amount of the amine is added to this solution. During this procedure, the salt is ordinarily obtained in the solid form, or it is isolated in a conventional manner after evaporation of the solvent.

The functional modification of the free OH-groups is carried out in accordance with methods known to those skilled in the art. For the introduction of the ether blocking groups, for example, the reaction is conducted with dihydropyran in methylene chloride or chloroform with the use of an acidic condensation agent, e.g. p-toluenesulfonic acid. The dihydropyran is utilized in an excess, preferably in 4 to 10 times the quantity of the theoretical requirement. The reaction is normally finished at 0° to 30° C. after 15–30 minutes.

The acyl blocking groups are introduced by conventionally reacting a compound of general Formula I with a carboxylic acid derivative, e.g. an acid chloride, an acid anhydride, and others.

Conventional methods are employed for liberating a functionally modified OH-group to obtain the compounds of general Formula I. For example, the splitting off of ether blocking groups is conducted in an aqueous solution of an organic acid, e.g. acetic acid, propionic acid, inter alia, or in an aqueous solution of an inorganic acid, e.g. hydrochloric acid. To improve the solubility, a water-miscible, inert organic solvent is suitably added. Organic solvents which can be used for this purpose are, for example, alcohols, e.g. methanol and ethanol, and ethers, e.g. dimethoxyethane, dioxane, and tetrahydrofuran. Tetrahydrofuran is preferably employed. The splitting off step is preferably effected at temperatures of between 20° and 80° C.

The saponification of the acyl groups takes place, for example, with alkali or alkaline earth carbonates or hydroxides in an alcohol or in the aqueous solution of an alcohol. Suitable alcohols are aliphatic alcohols, e.g. methanol, ethanol, butanol, etc., preferably methanol. Suitable alkali carbonates and hydroxides are potassium and sodium salts, but the potassium salts are preferred. Examples of suitable alkaline earth carbonates and hydroxides are calcium carbonate, calcium hydroxide, and barium carbonate. The reaction takes place at −10° to 70° C., preferably at 25° C.

The reaction of the compound of general Formula I with $R_2$ meaning a hydrogen atom with an isocyanate of general Formula III takes place optionally with the addition of a tertiary amine, e.g. triethylamine or pyridine. The reaction can be conducted without solvents or in an inert solvent, preferably acetonitrile, tetrahydrofuran, acetone, dimethylacetamide, methylene chloride, diethyl ether, benzene, toluene, dimethyl sulfoxide, at temperatures above or below room temperature, e.g. between −80° and 100° C., preferably at 0° to 30° C.

If the starting compound contains OH-groups in the prostane residue, these OH-groups are also made to react. If final products are desired in the final analysis which contain free hydroxy groups in the prostane residue, then starting compounds are suitably employed wherein such hydroxy groups are intermediarily blocked by ether or acyl residues which can preferably be split off easily.

The compounds of general Formula II serving as the starting material can be prepared, for example, by reacting, in a manner known per se, the THP-blocked ester of Formula V [T. Schaaf and E. J. Corey, J. Org. Chem. 37: 2921 (1972)]

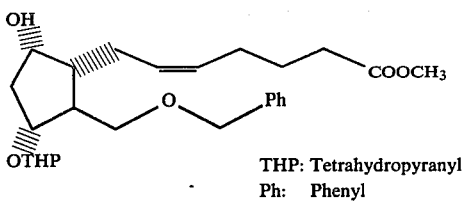

THP: Tetrahydropyranyl
Ph: Phenyl with mercury acetate or mercurcy trifluoroacetate, optionally in the presence of calcium carbonate in tetrahydrofuran, and subsequently reducing the intermediary mercury compound with sodium borohydride to obtain a compound of general Formula VI

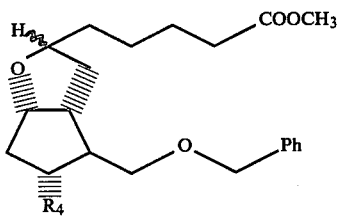

Thereafter, it is possible to split off the ether blocking group, if desired, by reaction with an organic acid, for example acetic acid, and optionally to react the thus-unblocked hydroxy group with a carboxylic acid derivative, e.g. an acid chloride, or an acid anhydride. The thus-obtained compounds of general Formula VI with $R_4$ having the above-indicated meanings can be optionally separated into the epimers by column chromatography or preparative layer chromatography.

After splitting of the benzyl ether by hydrogenolysis in the presence of a noble metal catalyst, for example palladium on charcoal, and subsequent oxidation of the primary hydroxy group, for example with Collins reagent, compounds of general Formula VII are obtained, wherein $R_4$ has the meanings indicated hereinabove:

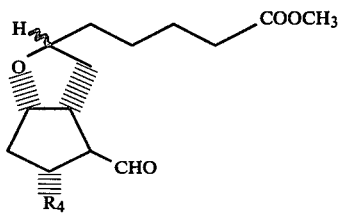

By subjecting the aldehyde of general Formula VII to an olefin-yielding reaction with a phosphorane of general Formula VIII

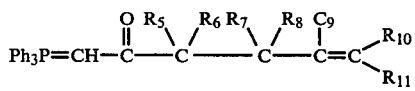

or a phosphonate of general Formula IX

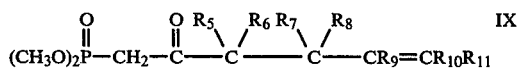

wherein $R_5$, $R_6$, $R_7$, $R_8$, $R_9$, $R_{10}$, and $R_{11}$ have the above-indicated meanings,
the ketone of general Formula II is obtained.

The compounds VIII and IX and the reaction with the aldehyde VII are described in W. S. Wadsworth and W. D. Emmons Org. Synthesis 45, 44 (1965), in E. J. Corey et al. JACS 90 3247 (1968) and in A. Maerker Org. Reactions 14, 270-490 (1965).

The compounds of general Formula IV can be prepared in accordance with DOS (German Unexamined Laid-Open Application) No. 2,729,960 and DOS' No. 2,635,985.

The novel prostane derivatives of general Formula I are valuable pharmaceuticals, since they exhibit, with a similar spectrum of activity, a substantially improved (higher specificity) and, above all, essentially prolonged effectiveness as contrasted with the corresponding natural prostaglandins. As compared to E-Prostaglandins, the novel prostaglandins are distinguished by a higher stability. The satisfactory tissue specificity of the novel prostaglandins is demonstrated in investigations on smooth-muscular organs, such as, for example, the guinea pig ileum or the isolated rabbit trachea, where a substantially lower stimulation is observed than when applying natural prostaglandins.

The novel prostaglandin analogs possess the pharmacological properties typical for prostacyclins, e.g. lowering of the peripheral arterial as well as coronary vascular resistance and therefore systemic blood pressure without decrease of cardiac output and coronary blood flow, inhibition of thrombocyte aggregation, suppression of gastric acid secretion, bronchospasmolysis, antiallergic properties, decrease of pulmonary vascular resistance and pulmonary blood pressure, increase of renal blood flow, increase of cerebral blood flow. Besides, the novel prostaglandin analogs possess antiprofilerative properties.

Upon intravenous injection carried out in nonanesthesized, hypertonic rats in doses of 20 μg. and 100 μg./kg. of body weight, the compounds of this invention show a stronger blood-pressure-lowering effect than PGE$_2$ and PGA$_2$, without triggering, as would PGE$_2$, at these dosages diarrhea or, as would PGA$_2$, cardiac arrhythmias.

Therefore, the compounds may be suitable for the following deseases:

Hypertension including essential hypertension, malignant hypertension and hypertensive emergencies, prevention of thrombosis and embolism e.g. in artheriosclerosis and postoperatively, treatment of hypertensive cases with myocardial injury infarction, coronary insufficiency and sclerosis, pulmonary hypertension, allergic and non-allergic bronchial constriction, renal insufficiency due to vascular dysfunction, disturbance of peripheral circulation including brain circulation; treatment of gastric and duodenal ulcers and psoriasis.

The novel prostaglandin analogs can be used for therapeutic treatment of hypertension in combination with other drugs commonly used in anti-hypertensive therapy, e.g. β-receptorblocker and diuretics.

For parenteral application, sterile, injectable, aqueous or oily solutions are utilized. The compounds may also be prepared as freeze dried material which is dissolved in appropriate solvent for injection.

Suitable for oral administration, for example, are tablets, dragees, or capsules, including retarded formulations of this type.

For local administration, the compounds are either inhaled (in aqueous solution, as dust: bronchoconstriction) or applied as ointments, lotions, jellies (scin).

Consequently, the invention also relates to medicinal agents on the basis of the compounds of general Formula I and customary auxiliary agents and vehicles.

The active agents of this invention are to serve, in conjunction with the excipients known and customary in galenic pharmacy, for example for the preparation of blood-pressure-lowering agents.

The pharmaceutically active compounds of Formula I can be processed in accordance with conventional methods of galenic pharmacy to produce medicinal agents, especially for oral administration. Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are solutions, preferably oily or aqueous solutions, as well as suspensions, emulsions, or implants, including suppositories. Ampoules are convenient unit dosages.

For enteral application, particularly suitable are tablets, dragees, or capsules having talc and/or a carbohydrate carrier or binder or the like, the carrier preferably being lactose and/or corn starch and/or potato starch. A syrup, elixir, or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–100 mg. in a pharmaceutically acceptable carrier per unit dosage.

| Use | Dosage mg/kg of body wt/day | Administration is analogous to that for the prior art agent listed below |
|---|---|---|
| Blood pressure lowering | 5–1000, preferably 20–250 | PGE$_2$, PGA$_2$ |
| Thrombocyte aggregation inhibition | 5–1000, preferably 20–250 | PGE$_1$ |
| Gastric acid secretion suppression | 5–1000, preferably 20–250 | PGE$_2$ |

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(1S,5R,6R,7R,3R)-7-Acetoxy-6-[(E)-(3S)-3-hydroxy-1-octen-6-ynyl]-3-(4-methoxycarbonyl-1-butyl)-2-oxabicyclo[3,3,0]octane At −40°, 420 mg. of sodium borohydride is added in incremental portions to a solution of 800 mg. of (1S,5R,6R,7R,3R)-7-acetoxy-6-[(E)-3-oxo-1-octen-6-ynyl]-3-(4-methoxycarbonyl-1-butyl)-2-oxabicyclo[3,3,0]octane in 24 ml. of methanol and 10 ml. of tetrahydrofuran. The mixture is agitated for 1 hour at −40°. Then the mixture is gently combined with 1 ml. of glacial acetic acid, concentrated under vacuum, the residue combined with methylene chloride, the organic extract shaken with 4% sodium bicarbonate solution, washed neutral with water, dried with magnesium sulfate, and evaporated under vacuum. After chromatography of the residue on silica gel with ether/pentane (6+4), 250 mg. of the corresponding compound in the β-configuration is obtained, along with 266 mg. of the title compound as a colorless oil.

IR (CHCl$_3$): 3650, 3450, 2960, 1732, 975 cm$^{-1}$.

The starting material for the above title compound is produced as follows:

1(a)

(1S,5R,6R,7R,3RS)-6-Benzyloxymethyl-3-(4-methoxycarbonyl-1-butyl)-7-(tetrahydropyran-2-yloxy)-2-oxabicyclo[3,3,0]octane 3.8 g. of mercury(II) acetate is added to a solution of 4.5 g. of the methyl ester of (9S,11R)-(5Z)-9-hydroxy-14-oxa-15-phenyl-11-(tetrahydropyran-2-yloxy)-16,17,18,19,20-pentanor-5-prostenoic acid [T. Schaaf and E. J. Corey, J. Org. Chem. 37: 2921 (1972)] in 140 ml. of tetrahydrofuran, and the mixture is stirred under argon at room temperature for 5 hours. Then the mixture is combined with 60 ml. of 1 N sodium hydroxide solution, stirred for 1 minute, a solution of 1.5 g. of sodium borohydride in 60 ml. of 1 N sodium hydroxide solution is added thereto, and the mixture is agitated for 5 minutes, whereupon it is diluted with ether, the organic phase shaken with water, dried with magnesium sulfate, and evaporated under vacuum. After chromatography on silica gel, pentane/ether (8+2) yields 3.3 g. of the title compound as a colorless oil.

IR: 2960, 1730 cm$^{-1}$.

1(b)

(1S,5R,6R,7R,3S)-6-Benzyloxymethyl-7-hydroxy-3-(4-methoxycarbonyl-1-butyl)-2-oxabicyclo[3,3,0]octane and (1S,5R,6R,7R,3R)-6-Benzyloxymethyl-7-hydroxy-3-(4-methoxycarbonyl-1-butyl)-2-oxabicyclo[3,3,0]octane 3.2 g. of the compound prepared according to Example 1(a) is agitated for 16 hours at room temperature with 80 ml. of a mixture of glacial acetic acid/water/THF (65/35/10), evaporated under vacuum, and the residue chromatographed on silica gel. With ether/pentane (7+3), 410 mg. of the compound having the 3S* configuration (4-methoxycarbonylbutyl chain in the β-position) is first obtained, and then, as the more polar fraction, 1.65 g. of the compound having the 3R* configuration (4-methoxycarbonylbutyl chain in the α-position) is obtained, both compounds as colorless oils.

IR (3S configuration): 3620, 3460, 2960, 2935, 1730 cm$^{-1}$.

IR (3R configuration): Spectrum almost identical to that of the 3S-configured compound.

(Note (*): The correlation of the configuration is not defined with absolute certainty. The determination of the configuration was made in analogy to the synthesis of 5,6-dihydro-PGI$_2$ [E. J. Corey et al., JACS 99: 2006 (1977)]. In the reference, the α-configuration is proposed for the product having the 4-methoxycarbonylbutyl chain in the polar primary product, while the β-configuration is suggested for the nonpolar secondary product.

1(c)
(1S,5R,6R,7R,3R)-7-Acetoxy-6-benzyloxymethyl-3-(4-methoxycarbonyl-1-butyl)-2-oxabicyclo[3,3,0]octane A solution of 1.5 g. of the 3R-configured compound (polar primary product) prepared according to Example 1(b) 1 ml. of acetic anhydride, and 3 ml. of pyridine is allowed to stand for 16 hours at room temperature and then concentrated under vacuum by evaporation, thus obtaining 1.7 g. of the title compound as an oil.

IR: 2960, 2935, 1732 cm$^{-1}$.

1(d)
(1S,5R,6R,7R,3R)-7-Acetoxy-6-hydroxymethyl-3-(4-methoxycarbonyl-1-butyl)-2-oxabicyclo[3,3,0]octane 4.8 g. of the compound produced according to Example 1(c) in 200 ml. of ethyl acetate and 50 ml. of ethanol is shaken with 0.9 g. of palladium (10% on charcoal) for 3 hours under a hydrogen atmosphere; the product is then filtered and evaporated under vaccum, thus obtaining 3.7 g. of the title compound as a colorless oil.

IR: 3620, 3450, 2960, 1732 cm$^{-1}$.

1(e)
(1S,5R,6R,7R,3R)-7-Acetoxy-6-formyl-3-(4-methoxycarbonyl-1-butyl)-2-oxabicyclo[3,3,0]octane At 0° a solution of 4 g. of the compound prepared according to Example 1(d) in 120 ml. of absolute methylene chloride is added to a solution of 30 g. of freshly prepared Collins reagent in 250 ml. of absolute methylene chloride. The mixture is stirred for 30 minutes, combined with 700 ml. of ether, and shaken in succession four times with respectively 40 ml. of 4% sodium bicarbonate solution, twice with respectively 40 ml. of 10% sulfuric acid, and four times with respectively 40 ml. of water. After drying over magnesium sulfate, the product is evaporated under vacuum, thus obtaining 3.2 g. of the title compound as a yellow oil.

IR: 2960, 2870, 2720, 1732 cm$^{-1}$.

1(f)
(1S,5R,6R,7R,3R)-7-Acetoxy-6-[(E)-3-oxo-1-octen-6-ynyl]-3-(4-methoxycarbonyl-1-butyl)2-oxabicyclo[3,3,0]octane At room temperature a solution of 530 mg. of 2-oxohept-5-ynephosphonic acid dimethyl ester (DOS 2,729,960) in 2 ml. of dimethoxyethane (DME) is added dropwise to a suspension of 96 mg. of sodium hydride (50% suspension in oil) in 10 ml. of DME; the mixture is stirred for 2 hours at 23° under argon and then combined at −20° with a solution of 620 mg. of the aldehyde prepared according to Example 1(e) in 6 ml. of DME. The mixture is then agitated for 1.5 hours at −10°, neutralized with acetic acid, diluted with ether, shaken with 4% sodium bicarbonate solution and water, dried over magnesium sulfate, and evaporated under vacuum. After purification by column chromatography on silica gel, ether/pentane (1+1) yields 654 mg. of the title compound as a colorless oil.

IR: 2960, 1730, 1690, 1632, 1245, 975 cm$^{-1}$.

EXAMPLE 2
(1S,5R,6R,7R,3R)-3-(4-Carboxy-1-butyl)-7-hydroxy-6-[(E)-(3S)-3-hydroxy-1-octen-6-ynyl]-2-oxabicyclo[3,3,0]octane 200 mg. of the compound prepared according to Example 1 is agitated for 16 hours at 25° with a solution of 300 mg. of sodium hydroxide in 10 ml. of methanol and 1.6 ml. of water. The mixture is then concentrated under vacuum, diluted with 5 ml. of brine, acidified to pH 5 with 10% citric acid solution, extracted three times with methylene chloride, the extract is shaken once with brine, dried over magnesium sulfate, and evaporated under vacuum. After filtration over a small amount of silica gel, with the use of chloroform/10% isopropanol, 140 mg. of the title compound is obtained in the form of an oil.

IR: 3600, 3450, 2960, 1710, 978 cm$^{-1}$.

EXAMPLE 3
(1S,5R,6R,7R,3S)-7-Acetoxy-6-[(E)-(3S)-3-hydroxy-1-octen-6-ynyl]-3-(4-methoxycarbonyl-1-butyl)-2-oxabicyclo[3,3,0]octane At −40°, 210 mg. of sodium borohydride is added in incremental portions to a solution of 390 mg. of (1S,5R,6R,7R,3S)-7-acetoxy-6-[(E)-3-oxo-1-octen-6-ynyl]-3-(4-methoxycarbonyl-1-butyl)-2-oxabicyclo[3,3,0]octane in 12 ml. of methanol and 5 ml. of tetrahydrofuran. The mixture is stirred for 1 hour at −40°, then combined with 0.5 ml. of glacial acetic acid, concentrated under vacuum, the residue mixed with methylene chloride, and the organic extract is shaken with 4% sodium bicarbonate solution and then washed neutral with water, dried over magnesium sulfate, and evaporated under vacuum. After chromatography of the residue on silica gel with ether/pentane (6+4), 110 mg. of the β-configured compound and 150 mg. of the title compound are obtained in the form of an oil.

IR (CHCl$_3$): 3640, 3460, 2960, 1732, 976 cm$^{-1}$.

The starting material for the above title compound is prepared as follows:

3(a)
(1S,5R,6R,7R,3S)-7-Acetoxy-6-benzyloxymethyl-3-(4-methoxycarbonyl-1-butyl)-2-oxabicyclo[3,3,0]octane A solution of 300 mg. of the 3S-configured compound (nonpolar secondary product) prepared according to Example 1(b), 0.3 ml. of acetic anhydride, and 1 ml. of pyridine is allowed to stand for 16 hours at room temperature and then evaporated under vacuum, thus obtaining 0.32 g. of the title compound as an oil.

IR: 2960, 2940, 1732, 1245 cm$^{-1}$.

3(b)
(1S,5R,6R,7R,3S)-7-Acetoxy-6-hydroxymethyl-3-(4-methoxycarbonyl-1-butyl)-2-oxabicyclo[3,3,0]octane Under a hydrogen atmosphere, 0.8 g. of the compound produced according to Example 3(a) in 30 ml. of ethyl acetate and 8 ml. of ethanol is shaken in 150 mg. of palladium (10% on charcoal) for 3 hours. The mixture is filtered and evaporated under vacuum, thus obtaining 610 mg. of the title compound as a colorless oil.

IR: 3600, 3450, 2960, 1732, 1245 cm$^{-1}$.

3(c)
(1S,5R,6R,7R,3S)-7-Acetoxy-6-formyl-3-(4-methoxycarbonyl-1-butyl)-2-oxabicyclo[3,3,0]octane At ice bath temperature, a solution of 1.9 g. of the compound prepared according to Example 3(b) in 50 ml. of absolute methylene chloride is added to a solution of 14 g. of freshly prepared Collins reagent in 120 ml. of absolute methylene chloride. The mixture is stirred for 30 minutes, combined with 350 ml. of ether, and shaken in sucession four times with respectively 20 ml. of 4% sodium bicarbonate solution, twice with respectively 30 ml. of water. After drying over magnesium sulfate, the mixture is evaporated under vacuum, thus obtaining 1.5 g. of the title compound as a yellowish oil.

IR: 2960, 2870, 2720, 1730 cm$^{-1}$.

3(d)
(1S,5R,6R,7R,3S)-7-Acetoxy-6-[(E)-3-oxo-1-octen-6-ynyl]-3-(4-methoxycarbonyl-1-butyl)-2-oxabicyclo[3,3,0]octane At room temperature a solution of 1.06 g. of the dimethyl ester of 2-oxohept-5-ynephosphonic acid (DOS No. 2,729,960) in 4 ml. of DME is added dropwise to a solution of 190 mg. of sodium hydride (50% suspension in oil) in 18 ml. of DME; the mixture is stirred for 2 hours at 22° under argon. Then, at −20°, the mixture is combined with a solution of 1.25 g. of the aldehyde prepared by following Example 3(c) in 10 ml. of DME, agitated for 2 hours at −10°, neutralized with acetic acid, diluted with ether, shaken with 4% sodium bicarbonate solution and water, dried over magnesium sulfate, and evaporated under vacuum. After column chromatography on silica gel, ether/pentane (1+1) yields 1.35 g. of the title compound as an oil.

IR: 2960, 1732, 1690, 1632, 1245, 975 cm$^{-1}$.

EXAMPLE 4
(1S,5R,6R,7R,3S)-3-(4-Carboxy-1-butyl)-7-hydroxy-6-[(E)-(3S)-3-hydroxy-1-octen-6-ynyl]-2-oxabicyclo[3,3,0]octane 150 mg. of the compound prepared according to Example 3 is agitated for 16 hours at 25° with a solution of 200 mg. of sodium hydroxide in 7 ml. of methanol and 1.2 ml. of water. The mixture is then concentrated under vacuum, diluted with 5 ml. of brine, acidified with 10% citric acid solution to pH 5, extracted three times with methylene chloride, the extract shaken once with brine, dried over magnesium sulfate, and evaporated under vacuum. After filtration over a small amount of silica gel, chloroform/10% isopropanol yields 95 mg. of the title compound as an oil.

IR: 3640, 3440, 2960, 1710, 978 cm$^{-1}$.

EXAMPLE 5
(1S,5R,6R,7R,3R)-7-Acetoxy-6-[(1E)-(3S)-3-hydroxy-b 7-methyl-1,6-octadienyl]-3-(4-methoxycarbonyl-1-butyl)-2-oxabicyclo[3,3,0]octane At −40°, 460 mg. of sodium borohydride is added in incremental portions to a solution of 900 mg. of (1S,5R,6R,7R,3R)-7-acetoxy-6-[(1E)-7-methyl-3-oxo-1,6-octadienyl]-3-(4-methoxycarbonyl-1-butyl)-2-oxabicyclo[3,3,0]octane in 28 ml. of methanol and 11 ml. of THF, and the mixture is stirred for 1 hour at −40°. Thereafter, the mixture is gently combined with 1 ml. of glacial acetic acid, concentrated under vacuum, combined with methylene chloride, the organic extract is shaken with 4% sodium bicarbonate solution, washed neutral withwater, dried over magnesium sulfate, and evaporated under vacuum. Chromatographic separation on silica gel yields, with ether/pentane (1+1), 270 mg. of the corresponding β-configured compound and 293 mg. of the title compound as a clear oil.

IR: 3640, 3450, 2960, 1732, 977 cm$^{-1}$.

The starting material for the above title compound is prepared as follows:

5(a)
(1S,5R,6R,7R,3R)-7-Acetoxy-6-[(1E)-7-methyl-3-oxo-1,6-octadienyl]-3-(4-methoxycarbonyl-1-butyl)-2-oxabicyclo[3,3,0]octane 3.1 g. of the aldehyde prepared in accordance with Example 1(e) and 4.2 g. of (6-methyl-2-oxo-5-heptenylidene)triphenylphosphorane (DOS No. 2,635,985.3) are dissolved in 80 ml. of absolute benzene and stirred under argon at room temperature for 7 hours. Thereafter, the reaction solution is concentrated to dryness with the use of a forced circulation evaporator, and the residue is purified by column chromatography on silica gel. With ether/pentane (1+1), 2.9 g. of the title compound is obtained as an oil.

IR: 2960, 1732, 1690, 1630, 1245, 976 cm$^{-1}$.

EXAMPLE 6
(1S,5R,6R,7R,3R)-3-(4-Carboxy-1-butyl)-7-hydroxy-6-[(1E)-(3S)-3-hydroxy-7-methyl-1,6-octadienyl]-2-oxabicyclo[3,3,0]octane At 25°, 220 mg. of the compound prepared according to Example 5 is agitated for 16 hours with a solution of 300 mg. of sodium hydroxide in 10 ml. of methanol and 1.6 ml. of water. The mixture is then concentrated under vacuum, diluted with 5 ml. of brine, acidified with 10% citric acid solution to pH 5, extracted three times with methylene chloride, the extract shaken once with brine, dried over magnesium sulfate, and evaporated under vacuum. After filtration over silica gel, 150 mg. of the title compound is obtained as an oil with chloroform/10% isopropanol.

IR: 3620, 3450, 2960, 1712, 978 cm$^{-1}$.

EXAMPLE 7
(1S,5R,6R,7R,3S)-7-Acetoxy-6-[(1E)-(3S)-3-hydroxy-7-methyl-1,6-octadienyl]-3-(4-methoxycarbonyl-1-butyl)-2-oxabicyclo[3,3,0]octane At −40°, 230 mg. of sodium borohydride is added in incremental portions to a solution of 470 mg. of (1S,5R,6R,7R,3S)-7-acetoxy-6-[(1E)-7-methyl-3-oxo-1,6-octadienyl]-3-(4-methoxycarbonyl-1-butyl)-2-oxabicyclo[3,3,0]octane in 14 ml. of methanol and 4 ml. of THF. The mixture is stirred for 1 hour at −40° and then combined with 0.6 ml. of glacial acetic acid, concentrated under vacuum, combined with methylene chloride, the organic extract shaken in 4% sodium bicarbonate solution, washed neutral with water, dried over magnesium sulfate, and evaporated under vacuum. After separation by chromatography on silica gel, ether/pentane (1+1) yields 120 mg. of the corresponding β-configured compound and 160 mg. of the title compound as a colorless oil.

IR: 3640, 3460, 2960, 1730, 978 cm$^{-1}$.

The starting material for the above title compound is produced as follows:

7(a)
(1S,5R,6R,7R,3S)-7-Acetoxy-6-[(1E)-7-methyl-3-oxo-1,6-octadienyl]-3-(4-methoxycarbonyl-1-butyl)-2-oxabicyclo[3,3,0]octane Analogously to Example 5(a), 1.58 g. of the aldehyde prepared according to Example 3(c) and 2.1 g. of (6-methyl-2-oxo-5-heptenylidene)triphenylphosphorane yield 1.4 g. of the title compound as an oil.

EXAMPLE 8
(1S,5R,6R,7R,3S)-3-(4-Carboxy-1-butyl)-7-hydroxy-6-[(E1)-(3S)-3-hydroxy-7-methyl-1,6-octadienyl]-2-oxabicyclo[3,3,0]octane In analogy to Example 6, 140 mg. of the compound prepared according to Example 7 yields 83 mg. of the title compound in the form of an oil.
IR: 3620, 3450, 2960, 1712, 978 cm$^{-1}$.

EXAMPLE 9
(1S,5R,6R,7R,3R)-7-Acetoxy-6-[(E)-(3RS)-3-hydroxy-3-methyl-1-octen-6-ynyl]-3-(4-methoxycarbonyl-1-butyl)-2-oxabicyclo[3,3,0]octane At −60°, 10 ml. of an ethereal methylmagnesium bromide solution (prepared from 0.05 mole of magnesium) is added dropwise to a solution of 3 g. of the ketone prepared according to Example 1(f) in 120 ml. of absolute tetrahydrofuran. The mixture is agitated for 30 minutes, then poured in 100 ml. of saturated ammonium chloride solution, agitated for 10 minutes at 20°, extracted four times with respectively 150 ml. of ether, the organic extract washed neutral with water, dried over magnesium sulfate, and evaporated under vacuum. After purification by column chromatography on silica gel, 2.6 g. of the title compound is obtained with ether/pentane (8+2) in the form of an oil.
IR: 3600, 3450, 2960, 1732, 975 cm$^{-1}$.

EXAMPLE 10
(1S,5R,6R,7R,3R)-3-(4-Carboxy-1-butyl)-7-hydroxy-6-[(E)-(3RS)-3-hydroxy-3-methyl-1-octen-6-ynyl]-2-oxabicyclo[3,3,0]octane Analogously to Example 2, 410 mg. of the compound produced according to Example 9 yields 305 mg. of the title compound as a colorless oil.
IR: 3600, 3450, 2960, 1710, 978 cm$^{-1}$.

EXAMPLE 11
(1S,5R,6R,7R,3S)-7-Acetoxy-6-[(E)-(3RS)-3-Hydroxy-3-methyl-1-octen-6-ynyl]-3-(4-methoxycarbonyl-1-butyl)-2-oxabicyclo[3,3,0]octane In analogy to Example 9, 0.9 g. of the ketone obtained according to Example 3(d) yields 0.68 g. of the title compound as an oil.
IR: 3600, 3440, 2960, 2940, 1732, 976 cm$^{-1}$.

EXAMPLE 12
(1S,5R,6R,7R,3S)-3-(4-Carboxy-1-butyl)-7-hydroxy-6-[(E)-(3RS)-3-hydroxy-3-methyl-1-octen-6-ynyl]-2-oxabicyclo[3,3,0]octane Analogously to Example 2, 380 mg. of the compound prepared by following Example 11 yields 288 mg. of the title compound in the form of an oil.
IR: 3600, 3450, 2960, 1710, 976 cm$^{-1}$.

EXAMPLE 13
(1S,5R,6R,7R,3R)-7-Acetoxy-6-[(1E)-(3RS)-3,7-dimethyl-3-hydroxy-1,6-octadienyl]-3-(4-methoxycarbonyl-1-butyl)-2-oxabicyclo[3,3,0]octane In analogy to Example 9, 0.8 g. of the ketone prepared in accordance with Example 5(a) yields 0.6 g. of the title compound as an oil.

EXAMPLE 14
(1S,5R,6R,7R,3R)-3-(4-Carboxy-1-butyl)-7-hydroxy-6-[(1E)-(3RS)-3,7-dimethyl-3-hydroxy-1,6-octadienyl]2-oxabicyclo[3,3,0]octane Analogously to Example 2, 320 mg. of the compound prepared as disclosed in Example 13 yields 245 mg. of the title compound in the form of an oil.
IR: 3600, 3440, 1710, 978 cm$^{-1}$.

EXAMPLE 15
(1S,5R,6R,7R,3S)-7-Acetoxy-6-[(1E)-(3RS)-3,7-dimethyl-3-hydroxy-1,6-octadienyl]-3-(4-methoxycarbonyl-1-butyl)-2-oxabicyclo[3,3,0]octane In analogy to Example 9, 0.6 g. of the ketone prepared by following Example 7(a) yields 0.46 g. of the title compound as an oil.

EXAMPLE 16
(1S,5R,6R,7R,3S)-3-(4-Carboxyl-butyl)-7-hydroxy-6-[(1E)-(3RS)-3,7-dimethyl-3-hydroxy-1,6-octadienyl]2-oxabicyclo[3,3,0]octane In analogy to Example 2, 0.4 g. of the compound prepared according to Example 15 yields 0.3 g. of the title compound in the form of an oil.
IR: 3620, 3450, 2965, 1710, 978 cm$^{-1}$.

EXAMPLE 17
(2S,5R,6R,7R,3R)-7-Acetoxy-6-[(E)-(3S,4RS)-3-hydroxy-4-methyl-1-octen-6-ynyl]-3-(4-methoxycarbonyl-1-butyl)-2-oxabicyclo[3,3,0]octane At −40°, 220 mg. of sodium borohydride is added in incremental portions to a solution of 440 mg. of the ketone produced according to Example 17(a) in 14 ml. of methanol and 5 ml. of THF; the mixture is stirred for 45 minutes at −40°. Then, the mixture is gently combined with 1 ml. of glacial acetic acid, concentrated under vacuum, the residue combined with methylene chloride, the organic extract shaken with 4% sodium bicarbonate solution, washed neutral with water, and evaporated under vacuum. After chromatography of the residue on silica gel, with the use of ether/pentane (6+4), 140 mg. of the corresponding β-configured compound is obtained as well as 155 mg. of the title compound as a colorless oil.
IR (CHCl$_3$): 3600, 3450, 2960, 1732, 976 cm$^{-1}$.

The starting material for the above title compound is prepared as set forth below:

17(a)
(1S,5R,6R,7R,3R)-7-Acetoxy-6-[(E)-(4RS)-4-methyl-3-oxo-1-octen-6-ynyl]-3-(4-methoxycarbonyl-1-butyl)-2-oxabicyclo[3,3,0]octane At room temperature a solution of 1.05 g. of 3-methyl-2-oxohept-5-ynephosphonic acid dimethyl ester (DOS No. 2,729,960) in 4 ml. of DME is added dropwise to a suspension of 192 mg. of sodium hydride (50% suspension in oil) in 20 ml. of DME. The mixture is stirred for 2 hours at 23° under argon, then combined at −20° with a solution of 1.24 g. of the aldehyde prepared according to Example 1(e) in 12 ml. of DME, agitated for 1.5 hours at −10°, neutralized with acetic acid, diluted with ether, shaken with 4% sodium bicarbonate solution and water, dried over magnesium sulfate, and evaporated under vacuum. After purification by column chromatography on silica gel, with ether/pentane (1+1), 1.31. g. of the title compound is obtained as an oil.

IR: 2960, 1730, 1690, 1630, 1245, 976 cm$^{-1}$.

EXAMPLE 18

(1S,5R,6R,7R,3R)-3-(4-Carboxy-1-butyl)-7-hydroxy-6-[(E)-(3S,4RS)-3-hydroxy-4-methyl-1-octen-6-ynyl]-2-oxabicyclo[3,3,0]octane Analogously to Example 2, 140 mg. of the compound obtained according to Example 17 yields 85 mg. of the title compound as a colorless oil.

IR: 3600, 3450, 2960, 1712, 978 cm$^{-1}$.

EXAMPLE 19

(1S,5R,6R,7R,3S)-7-Acetoxy-6-[(E)-(3S,4RS)-3-hydroxy-4-methyl-1-octen-6-ynyl]-3-(4-methoxycarbonyl-1-butyl)-2-oxabicyclo[3,3,0]octane At −40°, 420 mg. of sodium borohydride is added in incremental portions to a solution of 800 mg. of the ketone prepared according to Example 19(a) in 24 ml. of methanol and 10 ml. of THF, and the mixture is stirred for 1 hour at −40°. Thereafter, the mixture is gently combined with 1 ml. of glacial acetic acid, concentrated under vacuum, the residue combined with methylene chloride, the organic extract shaken with 4% sodium bicarbonate solution, washed neutral with water, and evaporated under vacuum. After chromatography of the residue, one obtains with ether/pentane (1+1) 230 mg. of the corresponding β-configured alcohol and 260 mg. of the title compound as a colorless oil.

IR: 3650, 3450, 2960, 1730, 978 cm$^{-1}$.

19(a)

(1S,5R,6R,7R,3S)-7-Acetoxy-6-[(E)-(4RS)-4-methyl-3-oxo-1-oxten-6-ynyl]-3-(4-methoxycarbonyl-1-butyl)-2-oxabicyclo[3,3,0]octane In analogy to Example 17(a), 0.55 g. of the dimethyl ester of 3-methyl-2-oxohept-5-ynephosphonic acid and 0.6 g. of the aldehyde prepared according to Example 3(e) yield 0.68 g. of the title compound as an oil.

EXAMPLE 20

(2S,5R,6R,7R,3S)-3-(4-Carboxy-1-butyl)-7-hydroxy-6-[(E)-(3S,4RS)-3-hydroxy-4-methyl-1-octen-6-ynyl]-2-oxabicyclo[3,3,0]octane Analogously to Example 2, 180 g. of the compound produced according to Example 19 yields 110 mg. of the title compound as a colorless oil.

IR: 3600, 3430, 2960, 1712, 976 cm$^{-1}$.

EXAMPLE 21

(1S,5R,6R,7R,3R)-7-Acetoxy-6-[(1E)-(3S,4RS)-4,7-dimethyl-3-hydroxy-1,6-octadienyl]-3-(4-methoxycarbonyl-1-butyl)-2-oxabicyclo[3,3,0]octane At −40°, 230 mg. of sodium borohydride is added in incremental portions to a solution of 440 mg. of the ketone prepared according to Example 21(a) in 14 ml. of methanol and 5 ml. of THF, and the mixture is stirred for 1 hour at −40°. Thereafter, the mixture is gently combined with 0.6 ml. of glacial acetic acid, concentrated under vacuum, combined with methylene chloride, the organic extract is shaken with 4% sodium bicarbonate solution, washed neutral with water, dried over magnesium sulfate, and evaporated under vacuum. After chromatographic separation on silica gel, one obtains with ether/pentane (1+1) 140 mg. of the corresponding β-configured compound and 145 mg. of the title compound in the form of an oil.

IR: 3600, 3450, 2960, 1732, 978 cm$^{-1}$.

The starting material for the above title compound is obtained as follows:

21(a)

(1S,5R,6R,7R,3R)-7-Acetoxy-6-[(1E)-(4RS)-4,7-dimethyl-3-oxo-1,6-octadienyl]-3-(4-methoxycarbonyl-1-butyl)-2-oxabicyclo[3,3,0]octane At 23° a solution of 550 mg. of the dimethyl ester of 2-oxo-3,6-dimethylhept-5-enephosphonic acid in 3 ml. of DME is added dropwise to a suspension of 100 mg. of sodium hydride (50% suspension in oil) in 8 ml. of dimethoxyethane. The mixture is agitated at 23° under argon for 2 hours. Thereafter, the mixture is combined at −20° with a solution of 620 mg. of the aldehyde prepared according to Example 1(e) in 6 ml. of DME, agitated for 1.5 hours at −10°, neutralized with acetic acid, diluted with ether, shaken with 4% sodium bicarbonate solution and water, dried over magnesium sulfate, and evaporated under vacuum. After purification by column chromatography on silica gel, with the use of ether/pentane (4+6), 590 mg. of the title compound is obtained as an oil.

IR: 2960, 1730, 1690, 1630, 1245, 976 cm$^{-1}$.

The phosphonate required for Example 21(a) is prepared as follows:

21(b) Dimethyl Ester of 2-Oxo-3,6-dimethylhept-5-enephosphonic Acid

At 24° a solution of 17 g. of the dimethyl ester of 2-oxobutylphosphonic acid in 60 ml. of THF is added dropwise to a suspension of 4.5 g. of sodium hydride (50% suspension in oil) in 160 ml. of absolute THF. The mixture is agitated for 1.5 hours and then at 24° 83 ml. of a 1.24-molar butyllithium solution in hexane is added dropwise to the reaction mixture. The latter is then stirred for 20 minutes, and then at 0° a solution of 15.5 g. of 4-bromo-2-methyl-2-butene in 40 ml. of absolute THF is added dropwise to this mixture. The mixture is stirred for 1 hour, neutralized with 3 N hydrochloric acid, and concentrated under vacuum, whereafter it is combined with 50 ml. of brine, extracted three times with respectively 100 ml. of methylene chloride, the organic extract shaken twice with respectively 50 ml. of brine, dried with magnesium sulfate, and evaporated under vacuum. After bulb tube distillation of the residue at 0.5 torr [mm. Hg] and 150°, 13.5 g. of the title compound is obtained as a colorless liquid.

IR: 3000, 2960, 2915, 2863, 1720, 1260, 1040 cm$^{-1}$.

EXAMPLE 22

(1S,5R,6R,7R,3R)-3-(4-Carboxy-1-butyl)-7-hydroxy-6-[(1E)-(3S,4RS)-4,7-dimethyl-3-hydroxy-1,6-octadienyl]2-oxabicyclo[3,3,0]octane Analogously to Example 2, 210 mg. of the compound prepared according to Example 21 yields 160 mg. of the title compound as an oil.

IR: 3640, 3450, 2960, 1710, 978 cm$^{-1}$.

EXAMPLE 23

(1S,5R,6R,7R,3S)-7-Acetoxy-6-[(1E)-(3S,4RS)-4,7-dimethyl-3-hydroxy-1,6-octadienyl]-3-(4-methoxycarbonyl-1-butyl)-2-oxabicyclo[3,3,0]octane At −40°, 420 mg. of sodium borohydride is added in incremental portions to a solution of 780 mg. of the ketone prepared as disclosed in Example 23(a) in 24 ml. of methanol and 8 ml. of THF. The mixture is stirred for 1 hour at −40° and then combined with 1 ml. of glacial acetic acid, concentrated under vacuum, the residue combined with methylene chloride, the organic extract shaken with 4% sodium bicarbonate solution, washed neutral with water, dried with magnesium sulfate, and evaporated under vacuum. After chromatography of the residue in silica gel, using ether/pentane (1+1), 260 mg. of the corresponding β-configured alcohol and 255 mg. of the title compound are obtained as an oil.

IR: 3600, 2960, 1732, 1245, 976 cm⁻¹.

The starting material for the above title compound is produced as follows:

23(a)

(1S,5R,6R,7R,3S)-7-Acetoxy-6-[(1E)-(4RS)-4,7-dimethyl-3-oxo-1,6-octadienyl]-3-(4-methoxycarbonyl-1-butyl)-2-oxabicyclo[3,3,0]octane Analogously to Example 21(a), 1.1 g. of the dimethyl ester of 2-oxo-3,6-dimethylhept-5-enephosphonic acid and 1.25 g. of the aldehyde prepared according to Example 3(e) yield 1.28 g. of the title compound as an oil.

EXAMPLE 24

(1S,5R,6R,7R,3S)-3-(4-Carboxy-1-butyl)-7-hydroxy-6-[(1E)-(3S,4RS)-4,7-dimethyl-3-hydroxy-1,6-octadienyl]-2-oxabicyclo[3,3,0]octane Analogously to Example 2, 290 mg. of the compound prepared according to Example 23 yields 190 mg. of the title compound as an oil.

EXAMPLE 25

(1S,5R,6R,7R,3R)-7-Acetoxy-6-[(E)-(3R)-4,4-dimethyl-3-hydroxy-1-octen-6-ynyl]-3-(4-methoxycarbonyl-1-butyl)-2-oxabicyclo[3,3,0]octane At −40°, 220 mg. of sodium borohydride is added to a solution of 410 mg. of the ketone produced according to Example 25(a) in 14 ml. of methanol and 5 ml. of THF. The mixture is stirred for 1 hour at −40°, then combined with 1 ml. of glacial acetic acid, concentrated under vacuum, and the residue combined with methylene chloride. The organic extract is shaken with 4% sodium bicarbonate solution, washed neutral with water, and evaporated under vacuum. After chromatography of the residue on silica gel, using ether/pentane (6+4), 123 mg. of the corresponding β-configured alcohol and 140 mg. of the title compound are obtained in the form of an oil.

IR: 3640, 3450, 2965, 1732, 978 cm⁻¹.

The starting material for the above title compound is obtained as set forth below:

25(a)

(1S,5R,6R,7R,3R)-7-Acetoxy-6-[(E)-4,4-dimethyl-3-oxo-1-octen-6-ynyl]-3-(4-methoxycarbonyl-1-butyl)-2-oxabicyclo[3,3,0]octane At 23° a solution of 1.1 g. of the dimethyl ester of 3,3-dimethyl-2-oxohept-5-ynephosphonic acid (DOS No. 2,729,960) in 4 ml. of DME is added dropwise to a suspension of 192 mg. of sodium hydride (50% suspension in oil) in 20 ml. of absolute DME. The mixture is stirred for 2 hours at 23° under argon, then combined at −20° with a solution of 1.24 g. of the aldehyde prepared according to Example 1(e) in 12 ml. of DME, stirred for 1.5 hours at −10°, neutralized with acetic acid, diluted with ether, shaken with 4% sodium bicarbonate solution and water, dried over magnesium sulfate, and evaporated under vacuum. After purification by column chromatography on silica gel, using ether/pentane (1+1), 1.28 g. of the title compound is obtained as a colorless oil.

EXAMPLE 26

(1S,5R,6R,7R,3R)-3-(4-Carboxy-1-butyl)-7-hydroxy-6-[(E)-(3R)-4,4-dimethyl-3-hydroxy-1-octen-6-ynyl]-2-oxabicyclo[3,3,0]octane Analogously to Example 2, 180 mg. of the compound produced according to Example 25 yields 120 mg. of the title compound as an oil.

IR: 3600, 3450, 2960, 1710, 976 cm⁻¹.

EXAMPLE 27

(1S,5R,6R,7R,3S)-7-Acetoxy-6-[(E)-(3R)-4,4-dimethyl-3-hydroxy-1-octen-6-ynyl]-3-(4-methoxycarbonyl-1-butyl)-2-oxabicyclo[3,3,0]octane At −40°, 210 mg. of sodium borohydride is added to a solution of 380 mg. of the ketone prepared as disclosed in Example 27(a) in 13 ml. of methanol and 4 ml. of THF, and the mixture is stirred for 1 hour at −40°, then combined with 1 ml. of glacial acetic acid, concentrated under vacuum, the residue combined with methylene chloride, the organic extract shaken with 4% sodium bicarbonate solution, washed neutral with water, and evaporated under vacuum. After separation of the remainder by chromatography on silica gel, with the use of ether/pentane (6+4), 143 mg. of the title compound is obtained as an oil.

IR: 3600, 3450, 2965, 1730, 976 cm⁻¹.

The starting material for the above title compound is prepared as follows:

27(a)

(1S,5R,6R,7R,3S)-7-Acetoxy-6-[(E)-4,4-dimethyl-3-oxo-1-octen-6-ynyl]-3-(4-methoxycarbonyl-1-butyl)-2-oxabicyclo[3,3,0]octane In analogy to Example 25(a), 0.6 g. of the dimethyl ester of 3,3-dimethyl-2-oxohept-5-ynephosphonic acid and 0.55 g. of the aldehyde produced by following Example 3(e) yield 0.59 g. of the title compound as an oil.

EXAMPLE 28

(1S,5R,6R,7R,3S)-3-(4-Carboxy-1-butyl)-7-hydroxy-6-[(E)-(3R)-4,4-dimethyl-3-hydroxy-1-octen-6-ynyl]-2-oxabicyclo[3,3,0]octane Analogously to Example 2, 160 mg. of the compound prepared according to Example 27 yields 105 mg. of the title compound in the form of an oil.

IR: 3610, 3450, 2965, 1710, 978 cm⁻¹.

EXAMPLE 29

(1S,5R,6R,7R,3R)-7-Acetoxy-6-[(1E)-(3R)-3-hydroxy-4,4,7-trimethyl-1,6-octadienyl]-3-(4-methoxycarbonyl-1-butyl)-2-oxabicyclo[3,3,0]octane At −40°, 230 mg. of sodium borohydride is added to a solution of 400 mg. of the ketone prepared according to Example 29(a) in 14 ml. of methanol and 4 ml. of THF, and the mixture is stirred for 1 hour at −40°. The mixture is then combined with 1 ml. of glacial acetic acid, concentrated under vacuum, combined with methylene chloride, shaken with 4% sodium bicarbonate solution, washed neutral with water, dried over magnesium sulfate, and evaporated under vacuum. After separation on silica gel by chromatography, using ether/pentane (6+4), 154 mg. of the title compound is obtained as a colorless oil.

The starting material for the above title compound is prepared as set forth below:

29(a)

(1S,5R,6R,7R,3R)-7-Acetoxy-6-[(1E)-3-oxo-4,4,7-trimethyl-1,6-octadienyl]-3-(4-methoxycarbonyl-1-butyl)-2-oxabicyclo[3,3,0]octane 1.6 g. of the aldehyde prepared according to Example 1(e) and 2.3 g. of (3,3,6-trimethyl-2-oxo-5-heptenylidene)triphenylphosphorane (DOS No. 2,635,985.3) in 40 ml. of absolute benzene is agitated for 16 hours at room temperature under argon. The reaction solution is thereupon evaporated and the residue purified by column chromatography on silica gel. With ether/pentane (1+1), 0.8 g. of the title compound is obtained in the form of an oil.

EXAMPLE 30

(1S,5R,6R,7R3R)-3-(4-Carboxy-1-butyl)-7-hydroxy-6-[(1E)-(3R)-3-hydroxy-4,4,7-trimethyl-1,6-octadienyl]-2-oxabicyclo[3,3,0]octane Analogously to Example 2, 130 mg. of the compound produced according to Example 29 yields 82 mg. of the title compound as an oil.

IR: 3600, 3400, 2965, 1710, 978 cm$^{-1}$.

EXAMPLE 31

(1S,5R,6R,7R,3S)-7-Acetoxy-6-[(1E)-(3R)-3-hydroxy-4,4,7-trimethyl-1,6-octadienyl]-3-(4-methoxycarbonyl-1-butyl)-2-oxabicyclo[3,3,0]octane At −40°, 230 mg. of sodium borohydride is added to a solution of 395 mg. of the ketone prepared as described in Example 31(a) in 14 ml. of methanol and 4 ml. of THF. The mixture is stirred for 1 hour at −40°, them combined with 1 ml. of glacial acetic acid, concentrated under vacuum, combined with methylene chloride, shaken with 4% sodium bicarbonate solution, washed neutral with water, dried over magnesium sulfate, and evaporated under vacuum. After separation by chromatography on silica gel, using ether/pentane (6+4), 133 mg. of the title compound is obtained in the form of an oil.

The starting material for the above title compound is obtained as follows:

31(a)

(1S,5R,6R,7R,3S)-7-Acetoxy-6-[(1E)-3-oxo-4,4,7-trimethyl-1,6-octadienyl]-3-(4-methoxycarbonyl-1-butyl)-2-oxabicyclo[3,3,0]octane Analogously to Example 29(a), 1.4 g. of the aldehyde prepared according to Example 3(e) yields 0.62 g. of the title compound in the form of an oil.

EXAMPLE 32

(1S,5R,6R,7R,3S)-3-(4-Carboxy-1-butyl)-7-hydroxy-6-[(1E)-(3R)-3-hydroxy-4,4,7-trimethyl-1,6-octadienyl]-2-oxabicyclo[3,3,0]octane Analogously to Example 2, 140 mg. of the compound prepared according to Example 31 yields 90 mg. of the title compound as an oil.

IR: 3640, 3400, 2965, 1710, 978 cm$^{-1}$.

EXAMPLE 33

(1S,5R,6R,7R,3R)-6-[(E)-(3S)-3-Hydroxy-1-octen-6-ynyl]-7-hydroxy-3-(4-methylsulfonylcarbamoyl-1-butyl)-2-oxabicyclo[3,3,0]octane 400 mg. of (1S,5R,6R,7R,3R)-3-(4-carboxy-1-butyl)-7-hydroxy-6-[(E)-(3S)-3-hydroxy-1-octen-6-ynyl]-2-oxabicyclo[3,3,0]octane (see Example 2), dissolved in 1 ml. of pyridine and 0.5 ml. of acetic anhydride, and 100 mg. of 4-dimethylaminopyridine are allowed to stand overnight at room temperature, then combined with 0.2 ml. of water, allowed to stand for two more hours, then diluted with 50 ml. of water, and extracted repeatedly with methylene chloride. The extract is shaken in succession with dilute sulfuric acid and brine, dried over magnesium sulfate, and evaporated under vacuum. The thus-obtained diacetate is dried under vacuum at 0.01 torr and 40° for 1 hour, then dissolved in 25 ml. of dry tetrahydrofuran, and combined with 1.5 ml. of triethylamine. To this solution is added dropwise 160 mg. of methanesulfonyl isocyanate, dissolved in 10 ml. of tetrahydrofuran, and the mixture is agitated for 6 hours at 20°. After neutralization with acetic acid, the mixture is concentrated by evaporation under vacuum, the residue is dissolved in 50 ml. of methylene chloride, shaken with saturated sodium bicarbonate solution and water, dried over magnesium sulfate, and evaporated under vacuum.

To split off the blocking group, the residue is stirred for 16 hours at 20° with a solution of 400 mg. of sodium hydroxide in 12 ml. of methanol and 2 ml. of water. Thereafter, the mixture is concentrated under vacuum, diluted with 15 ml. of brine, acidified to pH 5 with 10% citric acid solution, extracted repeatedly with methylene chloride, the extract is shaken with brine, dried over magnesium sulfate, and evaporated under vacuum. After chromatography of the residue over 10 g. of silica gel with chloroform/10% isopropanol, 185 mg. of the title compound is obtained in the form of an oil.

IR: 3600, 3380, 2945, 1720, 976 cm$^{-1}$.

EXAMPLE 34

(1S,5R,6R,7R,3S)-6-[(E)-(3S)-3-Hydroxy-1-octen-6-ynyl]-7-hydroxy-3-(4-methylsulfonylcarbamoyl-1-butyl)-2-oxabicyclo[3,3,0]octane By proceeding in accordance with Example 33, 340 mg. of (1S,5R,6R,7R,3S)-3-(4-carboxy-1-butyl)-7-hydroxy-6-[(E)-(3S)-3-hydroxy-1-octen-1-ynyl]-2- oxabicyclo[3,3,0]octane yields 90 mg. of the title compound.

IR: 3600, 3385, 2945, 1718, 976 cm$^{-1}$.

EXAMPLE 35

(1S,5R,6R,7R,3R)-6-[(1E)-(3S)-3-Hydroxy-7-methyl-1,6-octadien-1-yl]-7-hydroxy-3-(4-methylsulfonylcarbamoyl-1-butyl)-2-oxabicyclo[3,3,0]octane By following the procedure of Example 33, 400 mg. of (1S,5R,6R,7R,3R)-3-(4-carboxy-1-butyl)-7-hydroxy-6-[(1E)-(3S)-3-hydroxy-7-methyl-1,6-octadienyl]-2-oxabicyclo[3,3,0]octane (see Example 6) yields 210 of the title compound in the form of an oil.

IR: 3600, 3390, 2955, 1718, 978 cm$^{-1}$.

EXAMPLE 36

(1S,5R,6R,7R,3S)-6-[(1E)-(3S)-3-Hydroxy-7-methyl-1,6-octadien-1-yl]-7-hydroxy-3-(4-methylsulfonylcarbamoyl-1-butyl)-2-oxabicyclo[3,3,0]octane By proceeding in accordance with Example 33, 300 mg. of (1S,5R,6R,7R,3S)-3-(4-carboxy-1-butyl)-7-hydroxy-6-[(1E)-(3S)-3-hydroxy-7-methyl-1,6-octadienyl]-2-oxabicyclo[3,3,0]octane (see Example 8) yields 155 mg. of the title compound as an oil.

IR: 3610, 3485, 2955, 1720, 978 cm$^{-1}$.

EXAMPLE 37

(1S,5R,6R,7R,3R)-6-[(E)-(3R)-4,4-Dimethyl-3-hydroxy-1-octen-6-ynyl]-7-hydroxy-3-(4-methylsulfonylcarbamoyl-1-butyl)-2-oxabicyclo[3,3,0]octane By proceeding in accordance with Example 33, 300 mg. of (1S,5R,6R,7R,3R)-3-(4-carboxy-1-butyl)-7-hydroxy-6-[(E)-(3R)-4,4-dimethyl-3-hydroxy-1-octen-6-ynyl]-2-oxabicyclo[3,3,0]octane (see Example 26) yields 180 mg. of the title compound as an oil.

IR: 3600, 3480, 2955, 1718, 976 cm$^{-1}$.

By proceeding in accordance with Example 33, the corresponding methylsulfonylcarbamoyl compounds are produced from the carboxylic acids described in Examples 10, 12, 14, 16, 18, 20, 22, 24, 28, 30, and 32 by reaction with methanesulfonyl isocyanate.

EXAMPLE 38

(1S,5R,6R,7R,3R)-6-[(E)-(3S)-3-Hydroxy-1-octen-6-ynyl]-7-hydroxy-3-(4-isopropylsulfonylcarbamoyl-1-butyl)-2-oxabicyclo[3,3,0]octane A solution of 500 mg. of (1S,5R,6R,7R,3R)-3-(4-carboxy-1-butyl)-7-hydroxy-6-[(E)-(3S)-3-hydroxy-1-octen-6-ynyl]-2-oxabicyclo[3,3,0]octane (see Example 2), 100 mg. of 4-dimethylaminopyridine, and 0.5 ml. of acetic anhydride in 1 ml. of pyridine is allowed to stand for 4 hours at room temperature, combined with 0.2 ml. of water, agitated for 2 hours, diluted with 50 ml. of brine, and extracted repeatedly with methylene chloride. The extract is shaken with dilute sulfuric acid and brine, dried over magnesium sulfate, and evaporated under vacuum. The dried residue (1 hour at 40° and 0.01 torr) is dissolved in 25 ml. of dry tetrahydrofuran, and the solution is combined in succession with 1.5 ml. of triethylamine and a solution of 250 mg. of isopropylsulfonyl isocyanate in 15 ml. of tetrahydrofuran. The mixture is stirred for 6 hours at 20°, neutralized with acetic acid, and the solvent is removed by evaporation under vacuum. The residue is dissolved with 100 ml. of methylene chloride, the solution is shaken with saturated sodium bicarbonate solution and brine, dried over magnesium sulfate, and evaporated under vacuum.

To split off the acetate blocking groups, the residue is stirred for 16 hours at 20° with a solution of 450 mg. of sodium hydroxide in 14 ml. of methanol and 2 ml. of water. Thereafter, the mixture is concentrated under vacuum, diluted with 20 ml. of brine, acidified to pH 5 with 10% citric acid solution, extracted repeatedly with methylene chloride, the extract shaken with brine, dried over magnesium sulfate, and evaporated under vacuum. Chromatography on 10 g. of silica gel yields, with chloroform/10% isopropanol, 280 mg. of the title compound as an oil.

IR: 3600, 3385, 2960, 1720, 976 cm$^{-1}$.

EXAMPLE 39

(1S,5R,6R,7R,3R)-6-[(1E)-(3S)-3-Hydroxy-7-methyl-1,6-octadien-1-yl]-7-hydroxy-3-(4-isopropylsulfonylcarbamoyl-1-butyl)-2-oxabicyclo[3,3,0]octane By proceeding in accordance with Example 38, 300 mg. of (1S,5R,6R,7R,3R)-3-(4-carboxy-1-butyl)-7-hydroxy-6-[(1E)-(3S)-3-hydroxy-7-methyl-1,6-octadienyl]-2-oxabicyclo[3,3,0]octane (see Example 6) yields 145 mg. of the title compound in the form of an oil.

IR: 3600, 3485, 1715, 978 cm$^{-1}$.

EXAMPLE 40

(1S,5R,6R,7R,3R)-6-[(E)-(3RS)-3-Hydroxy-3-methyl-1-octen-6-ynyl]-7-hydroxy-3-(4-isopropylsulfonylcarbamoyl-1-butyl)-2-oxabicyclo[3,3,0]octane By proceeding in accordance with Example 38, 300 mg. of (1S,5R,6R,7R,3R)-3-(4-carboxy-1-butyl)-7-hydroxy-6-[(E)-(3RS)-3-hydroxy-3-methyl-1-octen-6-ynyl]-2-oxabicyclo[3,3,0]octane yields 180 mg. of the title compound as an oil.

IR: 3610, 3485, 1718, 978 cm$^{-1}$.

EXAMPLE 41

(1S,5R,6R,7R,3R)-6-[(E)-(3S,4RS)-3-Hydroxy-4-methyl-1-octen-6-ynyl]-7-hydroxy-3-(4-isopropylsulfonylcarbamoyl-1-butyl)-2-oxabicyclo[3,3,0]octane By proceeding in accordance with Example 38, 400 mg. of (1S,5R,6R,7R,3R)-3-(4-carboxy-1-butyl)-7-hydroxy-6-[(E)-(3S,4RS)-3-hydroxy-4-methyl-1-octen-6-ynyl]-2-oxabicyclo[3,3,0]octane (see Example 18) yields 230 mg. of the title compound as an oil.

IR: 3600, 3485, 2950, 1715, 976 cm$^{-1}$.

EXAMPLE 42

(1S,5R,6R,7R,3R)-6-[(E)-(3S,4RS)-4,7-Dimethyl-3-hydroxy-1,6-octadien-1-yl]-7-hydroxy-3-(4-isopropylsulfonylcarbamoyl-1-butyl)-2-oxabicyclo[3,3,0]octane In analogy to Example 38, 210 mg. of the carboxylic acid produced according to Example 22 yields 95 mg. of the title compound in the form of an oil.

IR: 3600, 3480, 2955, 1718, 976 cm$^{-1}$.

EXAMPLE 43

(1S,5R,6R,7R,3R)-6-[(E)-(3R)-4,4-Dimethyl-3-hydroxy-1-octen-6-ynyl]-7-hydroxy-3-(4-isopropylsulfonylcarbamoyl-1-butyl)-2-oxabicyclo[3,3,0]octane Analogously to Example 38, 400 mg. of the carboxylic acid prepared by following Example 26 yields 225 mg. of the title compound as an oil.

IR: 3600, 3480, 2950, 1715, 976 cm$^{-1}$.

EXAMPLE 44

(1S,5R,6R,7R,3R)-6-[(E)-3-Hydroxy-4,4,7-trimethyl-1,6-octadien-1-yl]-7-hydroxy-3-(4-isopropylsulfonylcarbamoyl-1-butyl)-2-oxabicyclo[3,3,0]octane In analogy to Example 38, 400 mg. of the carboxylic acid prepared according to Example 30 yields 205 mg. of the title compound in the form of an oil.

IR: 3600, 3480, 2950, 1718, 978 cm$^{-1}$.

By proceeding in accordance with Example 38 with the use of the carboxylic acids prepared as described in Examples 4, 8, 12, 14, 16, 20, 24, 28, and 32, the corresponding isopropylsulfonylcarbamoyl compounds are obtained.

EXAMPLE 45

(1S,5R,6R,7R,3R)-3-(4-Acetylcarbamoyl-1-butyl)-6-[(E)-(3S)-3-hydroxy-1-octen-6-ynyl]-7-hydroxy-2-oxabicyclo[3,3,0]octane 400 mg. of (1S,5R,6R,7R,3R)-3-(4-carboxy-1-butyl)-7-hydroxy-6-[(E)-(3S)-3-hydroxy-1-octen-6-ynyl]-2-oxabicyclo[3,3,0]octane, 100 mg. of 4-dimethylaminopyridine, 0.5 ml. of acetic anhydride, and 1 ml. of pyridine are stirred for 16 hours at 20°, then combined with 0.2 ml. of water, agitated for another 2 hours, diluted with 50 ml. of water, and extracted repeatedly with methylene chloride. The extract is shaken in succession with dilute sulfuric acid and brine, dried over magnesium sulfate, and evaporated under vacuum. The dried residue (1 hour at 40° and 0.01 torr) is dissolved in 15 ml. of acetonitrile and, at 0°, a solution of 150 mg. of acetylisocyanate in 10 ml. of acetonitrile is added dropwise thereto. The mixture is stirred for another 2 hours at 20°, concentrated under vacuum, acidified with dilute sulfuric acid to pH 5, extracted repeatedly with ether, and the extract washed neutral with brine, dried over magnesium sulfate, and evaporated under vacuum.

To split off the acetate blocking groups, the residue is stirred for 5 hours at 20° with a solution of 200 mg. of sodium hydroxide in 10 ml. of methanol and 1 ml. of water. Thereafter, the mixture is concentrated under vacuum, diluted with 20 ml. of brine, extracted repeatedly with methylene chloride, dried over magnesium sulfate, and evaporated under vacuum. The residue is purified by chromatography over 15 g. of silica gel. With chloroform/1-10% isopropanol, 295 mg. of the title compound is obtained as an oil.

IR: 3600, 3400, 2945, 1705, 976 cm$^{-1}$.

EXAMPLE 46

(1S,5R,6R,7R,3R)-3-(4-Acetylcarbamoyl-1-butyl)-6-[(E)-(3S)-3-hydroxy-7-methyl-1,6-octadien-7-yl]-7-hydroxy-2-oxabicyclo[3,3,0]octane In analogy to Example 45, 200 mg. of the carboxylic acid prepared according to Example 6 yields 120 mg. of the title compound as an oil.

IR: 3600, 3380, 2950, 1710, 978 cm$^{-1}$.

EXAMPLE 47

(1S,5R,6R,7R,3R)-3-(4-Acetylcarbamoyl-1-butyl)-6-[(E)-(3S,4RS)-3-hydroxy-4-methyl-1-octen-6-ynyl]-2-oxabicyclo[3,3,0]octane In analogy to Example 45, 200 mg. of the carboxylic acid prepared according to Example 18 yields 135 mg. of the title compound in the form of an oil.

IR: 3600, 3400, 2945, 1708, 978 cm$^{-1}$.

EXAMPLE 48

(1S,5R,6R,7R,3R)-3-(4-Acetylcarbamoyl-1-butyl)-6-[(E)-(3S,4RS)-4,7-dimethyl-3-hydroxy-1,6-octadien-1-yl]-7-hydroxy-2-oxabicyclo[3,3,0]octane In analogy to Example 45, 200 mg. of the carboxylic acid produced according to Example 22 yields 133 mg. of the title compound as an oil.

IR: 3600, 3400, 2955, 1710, 978 cm$^{-1}$.

EXAMPLE 49

(1S,5R,6R,7R,3R)-3-(4-Acetylcarbamoyl-1-butyl)-6-[(E)-(3R)-4,4-dimethyl-3-hydroxy-1-octen-6-ynyl]-7-hydroxy-2-oxabicyclo[3,3,0]octane Analogously to Example 45, 200 mg. of the compound prepared according to Example 26 yields 120 mg. of the title compound as an oil.

IR: 3600, 3400, 2955, 1708, 976 cm$^{-1}$.

EXAMPLE 50

(1S,5R,6R,7R,3R)-3-(4Acetylcarbamoyl-1-butyl)-6-[(E)-(3R)-3-hydroxy-4,4,7-trimethyl-1,6-octadien-1-yl]-7-hydroxy-2-oxabicyclo[3,3,0]octane Analogously to Example 45, 200 mg. of the carboxylic acid prepared by following Example 30 yields 130 mg. of the title compound as an oil.

IR: 3600, 3400, 2950, 1710, 976 cm$^{-1}$.

By proceeding in accordance with Example 45, the carboxylic acids prepared as described in Examples 4, 8, 10, 12, 14, 16, 20, 24, 28, and 32 are likewise converted into the acetylcarbamoyl compounds.

EXAMPLE 51

(1S,5R,6R,7R,3R)-3-(4-Methoxycarbonyl-1-butyl)-7-hydroxy-6-[(E)-(3R)-3-hydroxy-4,4,7-trimethyl-1,6-octadien-1-yl]-2-oxabicyclo[3,3,0]octane A solution of 100 mg. of the carboxylic acid prepared in Example 30 in 10 ml. of methylene chloride is combined dropwise with an ethereal diazomethane solution at 0° until the yellow coloring is permanent. After 5 minutes the mixture is evaporated under vacuum and the residue filtered with methylene chloride/2% isopropanol over silica gel, thus obtaining 95 mg. of the title compound as an oil.

IR: 3600, 3420, 2955, 1735, 978 cm$^{-1}$.

All other carboxylic acids described in the foregoing examples can be converted into the methyl esters in an analogous manner.

EXAMPLE 52

(1S,5R,6R,7R,3R)-3-(4-Carboxy-1-butyl)-7-hydroxy-6-[(E)-(3S)-3-hydroxy-1-octen-6-ynyl]-2-oxabicyclo[3,3,-0]octane Tris(hydroxymethyl)aminomethane Salt At 80° 0.05 ml. of a solution of tris(hydroxymethyl)aminomethane (production: 82.25 g. of the base is dissolved in 150 ml. of water) is added under agitation to a solution of 100 mg. of the carboxylic acid prepared according to Example 2 in 15 ml. of acetonitrile. The mixture is allowed to stand for 16 hours at room temperature, then filtered, the residue washed with 5 ml. of acetonitrile, dried under vacuum, and the yield is 80 mg. of the title compound as a white powder.

All other carboxylic acids described in the aforementioned examples can be converted in an analogous manner into their tris(hydroxymethyl)aminomethane salts.

EXAMPLE 53

(1S,5R,6R,7R,3R)-7-Hydroxy-6-[(E)-(3S)-3-hydroxy-7-methyl-1,6-octadien-1-yl]-3-(4-methoxycarbonyl-1-butyl)-2-oxabicyclo[3,3,0]octane (Polar Product)

and (1S,5R,6R,7R,3S)-7-Hydroxy-6-[(E)-(3S)-3-hydroxy-7-methyl-1,6-octadien-1-yl]-3-(4-methoxycarbonyl-1-butyl)-2-oxabicyclo[3,3,0]octane (Nonpolar Product)

A solution of 480 mg. of (5Z,13E)-(9S,11R,15S)-9,11,15-trihydroxy-19-methyl-5,13,18-prostatrienoic acid methyl ester (prepared according to DOS No. 2,635,985) and 530 mg. of mercury(II) acetate in 20 ml. of tetrahydrofuran is stirred with 200 mg. of pulverized calcium carbonate for 48 hours at 25°, and then combined in succession at 0° with 8 ml. of 1 N sodium hydroxide solution and a solution of 200 mg. of sodium borohydride in 8 ml. of 1 N sodium hydroxide solution. The mixture is stirred for 10 minutes and poured on 100 ml. of citrate buffer (pH 4), whereafter it is extracted three times with respectively 50 ml. of methylene chloride. The extract is shaken with sodium bicarbonate solution and brine, dried over magnesium sulfate, and evaporated under vacuum. The residue shows, in the thin-layer chromatogram in the system ether/dioxane (9+1), two spots which are more nonpolar as compared to the starting material. For purposes of purification, the product is chromatographed on silica gel with the use of a hexane/ethyl acetate gradient, thus obtaining 100 mg. of the nonpolar isomer and 210 mg. of the polar isomer, both in the form of oils.

IR (polar isomer): 3600, 3450, 2955, 1735, 978 cm$^{-1}$.

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A prostane derivative of the formula

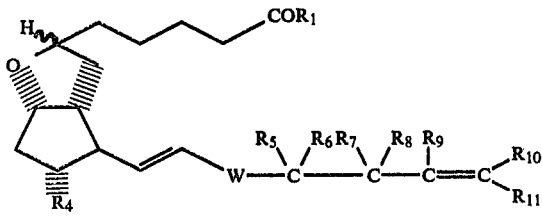

wherein
$R_1$ is $OR_2$ or $NHR_3$;
$R_2$ is hydrogen; $C_{1-10}$ alkyl; $C_{1-10}$ alkyl substituted by 1-3 of (a) halogen, (b) $C_{1-4}$ alkoxy, (c) $C_{6-10}$ aryl, (d) $C_{6-10}$ aryl substituted by 1-3 halogen atoms, phenyl, 1-3 $C_{1-4}$ alkyl groups, chloromethyl, fluoromethyl, trifluoromethyl, carboxyl, hydroxy or $C_{1-4}$ alkoxy, (e) di-$C_{1-4}$-alkyl amino or (f) tri-$C_{1-4}$-alkyl ammonium; $C_{4-10}$ cycloalkyl; $C_{4-10}$ cycloalkyl substituted by $C_{1-4}$ alkyl, the total number of C-atoms being 4-10; $C_{6-10}$ aryl; $C_{6-10}$ aryl substituted by 1-3 halogen atoms, phenyl, 1-3 $C_{1-4}$ alkyl groups, chloromethyl, fluoromethyl, trifluoromethyl, carboxyl, hydroxy or $C_{1-4}$ alkoxy; or a 5 or 6 membered heterocyclic ring having one hetero atom selected from O, N and S;
$R_3$ is the acyl residue of a hydrocarbon carboxylic or sulfonic acid of 1-15 carbon atoms;
W is (a) an OH-substituted methylene group, (b) a

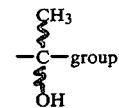

group wherein the OH-groups in (a) or (b) can be in the α- or β-position, or (c) such a group wherein the H atom of the OH group is replaced by the acyl residue of a hydrocarbon carboxylic or sulfonic acid of 1-15 carbon atoms or by a conventional etherifying OH-blocking group selected from tetrahydropyranyl, tetrahydrofuranyl, α-ethoxyethyl, trimethylsilyl, dimethyl-tert-butylsilyl and tri-p-benzylsilyl;
$R_4$ is OH or hydroxy whose H atom is replaced as defined for W; and
$R_5$, $R_6$, $R_7$, $R_8$, $R_9$, $R_{10}$ and $R_{11}$ each independently is hydrogen or alkyl of 1-5 carbon atoms; or $R_9$ and $R_{10}$ together represent a direct bond; and when $R_{11}$ is alkyl, $R_{10}$ can also be chlorine;
and for a derivative wherein $R_2$ is hydrogen, the salts thereof with physiologically compatible bases.

2. (1S,5R,6R,7R,3R)-7-Acetoxy-6-[(E)-(3S)-3-hydroxy-1-octen-6-ynyl]-3-(4-methoxycarbonyl-1-butyl)-2-oxabicyclo[3,3,0]octane, a compound of claim 1.

3. (1S,5R,6R,7R,3R)-3-(4-Carboxy-1-butyl)-7-hydroxy-6-[(E)-(3S)-3-hydroxy-1-octen-6-ynyl]-2-oxabicyclo[3,3,0]octane, a compound of claim 1.

4. (1S,5R,6R,7R,3S)-7-Acetoxy-6-[(E)-(3S)-3-hydroxy-1-octen-6-ynyl]-3-(4-methoxycarbonyl-1-butyl)-2-oxabicyclo[3,3,0]octane, a compound of claim 1.

5. (1S,5R,6R,7R,3S)-3-(4-Carboxy-1-butyl)-7-hydroxy-6-[(E)-(3S)-3-hydroxy-1-octen-6-ynyl]-2-oxabicyclo[3,3,0]octane, a compound of claim 1.

6. (1S,5R,6R,7R,3R)-7-Acetoxy-6-[(1E)-(3S)-3-hydroxy-7-methyl-1,6-octadienyl]-3-(4-methoxycarbonyl-1-butyl)-2-oxabicyclo[3,3,0]octane, a compound of claim 1.

7. (1S,5R,6R,3R)-3-(4-Carboxy-1-butyl)-7-hydroxy-6-[(1E)-(3S)-3-hydroxy-7-methyl-1,6-octadienyl]-2-oxabicyclo[3,3,0]octane, a compound of claim 1.

8. (1S,5R,6R,7R,3S)-7-Acetoxy-6-[(1E)-(3S)-3-hydroxy-7-methyl-1,6-octadienyl]-3-(4-methoxycarbonyl-1-butyl)-2-oxabicyclo[3,3,0]octane, a compound of claim 1.

9. (1S,5R,6R,7R,3S)-3-(4-Carboxy-1-butyl)-7-hydroxy-6-[(1E)-(3S)-3-hydroxy-7-methyl-1,6-octadienyl]-2-oxabicyclo[3,3,0]octane, a compound of claim 1.

10. (1S,5R,6R,3R)-7-Acetoxy-6-[(E)-(3RS)-3-hydroxy-3-methyl-1-octen-6-ynyl]-3-(4-methoxycarbonyl-1-butyl)-2-oxabicyclo[3,3,0]octane, a compound of claim 1.

11. (1S,5R,7R,3R)-3-(4-Carboxy-1-butyl)-7-hydroxy-6-[(E)-(3RS)-3-hydroxy-3-methyl-1-octen-6-ynyl]-2-oxabicyclo[3,3,0]octane, a compound of claim 1.

12. (1S,5R,6R,7R,3S)-7-Acetoxy-6-[(E)-(3RS)-3-hydroxy-3-methyl-1-octen-6-ynyl]-3-(4-methoxycarbonyl-1-butyl)-2-oxabicyclo[3,3,0]octane, a compound of claim 1.

13. (1S,5R,6R,3S)-3-(4-Carboxy-1-butyl)-7-hydroxy-6-[(E)-(3RS)-3-hydroxy-3-methyl-1-octen-6-ynyl]-2-oxabicyclo[3,3,0]octane, a compound of claim 1.

14. (1S,5R,6R,7R,3R)-7-Acetoxy-6-[(1E)-(3RS)-3,7-dimethyl-3-hydroxy-1,6-octadienyl]-3-(4-methoxycarbonyl-1-butyl)-2-oxabicyclo[3,3,0]octane, a compound of claim 1.

15. (1S,5R,7R,3R)-3-(4-Carboxy-1-butyl)-7-hydroxy-6-[(1E)-(3RS)-3,7-dimethyl-3-hydroxy-1,6-octadienyl]-2-oxabicyclo[3,3,0]octane, a compound of claim 1.

16. (1S,5R,6R,3S)-7-Acetoxy-6-[(1E)-(3RS)-3,7-dimethyl-3-hydroxy-1,6-octadienyl]-3-(4-methoxycarbonyl-1-butyl)-2-oxabicyclo[3,3,0]octane, a compound of claim 1.

17. (1S,5R,6R,7R,3S)-3-(4-Carboxy-1-butyl)-7-hydroxy-6-[(1E)-(3RS)-3,7-dimethyl-3-hydroxy-1,6-octadienyl]-2-oxabicyclo[3,3,0]octane, a compound of claim 1.

18. (1S,5R,6R,7R,3R)-7-Acetoxy-6-[(E)-(3S,4RS)-3-hydroxy-4-methyl-1-octen-6-ynyl]-3-(4-methoxycarbonyl-1-butyl)-2-oxabicyclo[3,3,0]octane, a compound of claim 1.

19. (1S,5R,6R,7R,3R)-3-(4-Carboxy-1-butyl)-7-hydroxy-6-[(E)-(3S,4RS)-3-hydroxy-4-methyl-1-octen-6-ynyl]-2-oxabicyclo[3,3,0]octane, a compound of claim 1.

20. (1S,5R,6R,3S)-7-Acetoxy-6-[(E)-(3S,4RS)-3-hydroxy-4-methyl-1-octen-6-ynyl]-3-(4-methoxycarbonyl-1-butyl)-2-oxabicyclo[3,3,0]octane, a compound of claim 1.

21. (1S,5R,6R,7R,3S)-3-(4-Carboxy-1-butyl)-7-hydroxy-6-[(E)-(3S,4RS)-3-hydroxy-4-methyl-1-octen-6-ynyl]-2-oxabicyclo[3,3,0]octane, a compound of claim 1.

22. (1S,5R,6R,7R,3R)-7-Acetoxy-6-[(1E)-(3S,4RS)-4,7-dimethyl-3-hydroxy-1,6-octadienyl]-3-(4-methoxycarbonyl-1-butyl)-2-oxabicyclo[3,3,0]octane, a compound of claim 1.

23. (1S,5R,6R,7R,3R)-3-(4-Carboxy-1-butyl)-7-hydroxy-6-[(1E)-(3S,4RS)-4,7-dimethyl-3-hydroxy-1,6-octadienyl]-2-oxabicyclo[3,3,0]octane, a compound of claim 1.

24. (1S,5R,6R,7R,3S)-7-Acetoxy-6-[(1E)-(3S,4RS)-4,7-dimethyl-3-hydroxy-1,6-octadienyl]-3-(4-methoxycarbonyl-1-butyl)-2-oxabicyclo[3,3,0]octane, a compound of claim 1.

25. (1S,5R,6R,7R,3S)-3-(4-Carboxy-1-butyl)-7-hydroxy-6-[(1E)-(3S,4RS)-4,7-dimethyl-3-hydroxy-1,6-octadienyl]-2-oxabicyclo[3,3,0]octane, a compound of claim 1.

26. (1S,5R,6R,7R,3R)-7-Acetoxy-6-[(E)-(3R)-4,4-dimethyl-3-hydroxy-1-octen-6-ynyl]-3-(4-methoxycarbonyl-1-butyl)-2-oxabicyclo[3,3,0]octane, a compound of claim 1.

27. (1S,5R,6R,7R,3R)-3-(4-Carboxy-1-butyl)-7-hydroxy-6-[(E)-(3R)-4,4-dimethyl-3-hydroxy-1-octen-6-ynyl]-2-oxabicyclo[3,3,0]octane, a compound of claim 1.

28. (1S,5R,6R,3S)-7-Acetoxy-6-[(E)-(3R)-4,4-dimethyl-3-hydroxy-1-octen-6-ynyl]-3-(4-methoxycarbonyl-1-butyl)-2-oxabicyclo[3,3,0]octane, a compound of claim 1.

29. (1S,5R,6R,7R,3S)-3-(4-Carboxy-1-butyl)-7-hydroxy-6-[(E)-(3R)-4,4-dimethyl-3-hydroxy-1-octen-6-ynyl]-2-oxabicyclo[3,3,0]octane, a compound of claim 1.

30. (1S,5R,6R,7R,3R)-7-Acetoxy-6-[(1E)-(3R)-3-hydroxy-4,4,7-trimethyl-1,6-octadienyl]-3-(4-methoxycarbonyl-1-butyl)-2-oxabicyclo[3,3,0]octane, a compound of claim 1.

31. (1S,5R,6R,7R,3R)-3-(4-Carboxy-1-butyl)-7-hydroxy-6-[(1E)-(3R)-3-hydroxy-4,4,7-trimethyl-1,6-octadienyl]-2-oxabicyclo[3,3,0]octane, a compound of claim 1.

32. (1S,5R,6R,7R,3S)-7-Acetoxy-6-[(1E)-(3R)-3-hydroxy-4,4,7-trimethyl-1,6-octadienyl]-3-(4-methoxycarbonyl-1-butyl)-2-oxabicyclo[3,3,0]octane, a compound of claim 1.

33. (1S,5R,7R,3S)-3-(4-Carboxy-1-butyl)-7-hydroxy-6-[(1E)-(3R)-3-hydroxy-4,4,7-trimethyl-1,6-octadienyl]-2-oxabicyclo[3,3,0]octane, a compound of claim 1.

34. (1S,5R,6R,7R,3S)-6-[(E)-(3S)-3-Hydroxy-1-octen-6-ynyl]-7-hydroxy-3-(4-methylsulfonylcarbamoyl-1-butyl)-2-oxabicyclo[3,3,0]octane, a compound of claim 1.

35. (1S,5R,6R,7R,3S)-6-[(E)-(3S)-3-Hydroxy-1-octen-6-ynyl]-7-hydroxy-3-(4-methylsulfonylcarbamoyl-1-butyl)-2-oxabicyclo[3,3,0]octane, a compound of claim 1.

36. (1S,5R,6R,7R,3R)-6-[(E)-(3S)-3-Hydroxy-7-methyl-1,6-octadien-1-yl]-7-hydroxy-3-(4-methylsulfonylcarbamoyl-1-butyl)-2-oxabicyclo[3,3,0]octane, a compound of claim 1.

37. (1S,5R,6R,7R,3S)-6-[(E)-(3S)-3-Hydroxy-7-methyl-1,6-octadien-1-yl]-7-hydroxy-3-(4-methylsulfonylcarbamoyl-1-butyl)-2-oxabicyclo[3,3,0]octane, a compound of claim 1.

38. (1S,5R,6R,7R,3R)-6-[(E)-(3R)-4,4-Dimethyl-3-hydroxy-1-octen-6-ynyl]-7-hydroxy-3-(4-methylsulfonylcarbamoyl-1-butyl)-2-oxabicyclo[3,3,0]octane, a compound of claim 1.

39. (1S,5R,6R,7R,3R)-6-[(E)-(3S)-3-Hydroxy-1-octen-6-ynyl]-7-hydroxy-3-(4-isopropylsulfonylcarbamoyl-1-butyl)-2-oxabicyclo[3,3,0]octane, a compound of claim 1.

40. (1S,5R,6R,7R,3R)-6-[(E)-(3S)-3-Hydroxy-7-methyl-1,6-octadien-1-yl]-7-hydroxy-3-(4-isopropylsulfonylcarbamoyl-1-butyl)-2-oxabicyclo[3,3,0]octane, a compound of claim 1.

41. (1S,5R,6R,7R,3R)-6-[(E)-(3RS)-3-Hydroxy-3-methyl-1-octen-6-ynyl]-7-hydroxy-3-(4-isopropylsulfonylcarbamoyl-1-butyl)-2-oxabicyclo[3,3,0]octane, a compound of claim 1.

42. (1S,5R,6R,7R,3R)-6-[(E)-(3S,4RS)-3-Hydroxy-4-methyl-1-octen-6-ynyl]-7-hydroxy-3-(4-isopropylsulfonylcarbamoyl-1-butyl)-2-oxabicyclo[3,3,0]octane, a compound of claim 1.

43. (1S,5R,6R,7R,3R)-6-[(E)-(3S,4RS)-4,7-Dimethyl-3-hydroxy-1,6-octadien-1-yl]-7-hydroxy-3-(4-isopropylsulfonylcarbamoyl-1-butyl)-2-oxabicyclo[3,3,0]octane, a compound of claim 1.

44. (1S,5R,6R,7R,3R)-6-[(E)-(3R)-4,4-Dimethyl-3-hydroxy-1-octen-6-ynyl]-7-hydroxy-3-(4-isopropylsulfonylcarbamoyl-1-butyl)-2-oxabicyclo[3,3,0]octane, a compound of claim 1.

45. (1S,5R,6R,3R)-6-[(E)-(3R)-3-Hydroxy-4,4,7-trimethyl-1,6-octadien-1-yl]-7-hydroxy-3-(4-isopropylsulfonylcarbamoyl-1-butyl)-2-oxabicyclo[3,3,0]octane, a compound of claim 1.

46. (1S,5R,6R,7R,3R)-3-(4-Acetylcarbamoyl-1-butyl)-6-[(E)-(3S)-3-hydroxy-1-octen-6-ynyl]-7-hydroxy-2-oxabicyclo[3,3,0]octane, a compound of claim 1.

47. (1S,5R,6R,7R,3R)-3-(4-Acetylcarbamoyl-1-butyl)-6-[(E)-(3S)-3-hydroxy-7-methyl-1,6-octadien-1- yl]-7-hydroxy-2-oxabicyclo[3,3,0]octane, a compound of claim 1.

48. (1S,5R,6R,7R,3R)-3-(4-Acetylcarbamoyl-1-butyl)-6-[(E)-(3S,4RS)-3-hydroxy-4-methyl-1-octen-6-ynyl]-2-oxabicyclo[3,3,0]octane, a compound of claim 1.

49. (1S,5R,6R,7R,3R)-3-(4-Acetylcarbamoyl-1-butyl)-6-[(E)-(3S,4RS)-4,7-dimethyl-3-hydroxy-1,6-octadien-1-yl]-7-hydroxy-2-oxabicyclo[3,3,0]octane, a compound of claim 1.

50. (1S,5R,6R,7R,3R)-3-(4-Acetylcarbamoyl-1-butyl)-6-[(E)-(3R)-4,4-dimethyl-3-hydroxy-1-octen-6ynyl]-7-hydroxy-2-oxabicyclo[3,3,0]octane, a compound of claim 1.

51. (1S,5R,6R,7R,3R)-3-(4-Acetylcarbamoyl-1-butyl)-6-[(E)-(3R)-3-hydroxy-4,4,7-trimethyl-1,6-octadien-1-yl]-7-hydroxy-2-oxabicyclo[3,3,0]octane, a compound of claim 1.

52. (1S,5R,6R,7R,3R)-3-(4-Methoxycarbonyl-1-butyl)-7-hydroxy-6-[(E)-(3R)-3-hydroxy-4,4,7-trimethyl-1,6-octadien-1-yl]-2-oxabicyclo[3,3,0]octane, a compound of claim 1.

53. (1S,5R,6R,3R)-3-(4-Carboxy-1-butyl)-7-hydroxy-6-[(E)-(3S)-3-hydroxy-1-octen-6-ynyl]-2-oxabicyclo[3,3,0]octane tris(hydroxymethyl)aminomethane salt, a compound of claim 1.

54. (1S,5R,6R,7R,3R)-7-Hydroxy-6-[(E)-(3S)-3-hydroxy-7-methyl-1,6-octadien-1-yl]-3-(4-methoxycarbonyl-1-butyl)-2-oxabicyclo[3,3,0]octane (polar product) and (1S,5R,6R,7R,3S)-7-Hydroxy-6-[(E)-(3S)-3-hydroxy-7-methyl-1,6-octadien-1-yl]-3-(4-methoxycarbonyl-1-butyl)-2-oxabicyclo[3,3,0]octane (nonpolar product), both compounds of claim 1.

55. A pharmaceutical composition comprising an amount of a compound of claim 1 effective to lower blood pressure and a pharmaceutically acceptable carrier.

56. A method of lowering blood pressure which comprises administering an amount of a compound of claim 1 effective to lower blood pressure.

57. A method of inhibiting thrombocyte aggregation which comprises administering an amount of a compound of claim 1 effective to inhibit thrombocyte aggregation.

58. A method of suppressing gastric acid secretion which comprises administering an amount of a compound of claim 1 effective to suppress gastric acid secretion.

59. A method of regulating heart rhythm which comprises administering an amount of a compound of claim 1 effective to regulate heart rhythm.

60. A method of promoting diuresis which comprises administering an amount of a compound of claim 1 effective to promote diuresis.

* * * * *